US011781175B1

(12) United States Patent
Steyaert et al.

(10) Patent No.: US 11,781,175 B1
(45) Date of Patent: Oct. 10, 2023

(54) PCR-BASED EPIGENETIC AGE PREDICTION

(71) Applicant: H42, INC., Waarloos (BE)

(72) Inventors: Sandra Ann R Steyaert, San Diego, CA (US); Geert Trooskens, Meise (BE); Wim Maria R. Van Criekinge, Waarloos (BE); Adriaan Verhelle, San Diego, CA (US); Johan Irma H. Vandersmissen, Hoeselt (BE)

(73) Assignee: H42, INC., Waarloos (BE)

( * ) Notice: Subject to any disclaimer, the term of this patent is extended or adjusted under 35 U.S.C. 154(b) by 0 days.

(21) Appl. No.: 17/831,427

(22) Filed: Jun. 2, 2022

(51) Int. Cl.
*C12Q 1/6876* (2018.01)
*C12Q 1/6844* (2018.01)
*C12Q 1/6806* (2018.01)

(52) U.S. Cl.
CPC ......... *C12Q 1/6844* (2013.01); *C12Q 1/6806* (2013.01); *C12Q 1/6876* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 10,435,743 B2 | 10/2019 | Vilain et al. | |
| 2015/0259742 A1 | 9/2015 | Zhang et al. | |
| 2017/0175205 A1 | 6/2017 | Toung et al. | |
| 2018/0274039 A1 | 9/2018 | Zhang et al. | |
| 2019/0185938 A1* | 6/2019 | Horvath | C12Q 1/6827 |
| 2020/0190568 A1 | 6/2020 | Boroni Martins et al. | |
| 2020/0261391 A1 | 8/2020 | Soni et al. | |

FOREIGN PATENT DOCUMENTS

EP 2711431 A1 3/2014

OTHER PUBLICATIONS

Varley, Bisulfite Patch PCR enables multiplexed sequencing of promoter methylation across cancer samples, Genome Res., 20: 1279-1287, 2010. (Year: 2010).*
Fitzgerald et al., Potential reversal of epigenetic age using a diet and lifestyle intervention: a pilot randomized clinical trial, Apr. 12, 2021, Aging 2-21 vol. 13 No. 7, 14 pages.
Jaganathan et al., Predicting splicing from primary sequence with deep learning, Cell Press, dated Jan. 24, 2019, 40 pages.
Hannum et al., Genome-wide Methylation Profiles Reveal Quantitative Views of Human Aging Rates, Molecular Cell Resource 49, pp. 359-367, dated Jan. 24, 2013, 9 pages.
Horvath, DNA methylation age of human tissues and cell types, Genome Biology, dated 2013, 20 pages.
Vidaki, Athina, et al. "DNA methylation-based forensic age prediction using artificial neural networks and next generation sequencing", Forensic Science Interanational: Genetics, Elsever BV, NE, vol. 28, Feb. 28, 2017, pp. 225-236.
PCT/IB2022/060944—International Search Report and Written Opinion dated Feb. 1, 2023, pp. 1-13 [downloaded from ePCT Jan. 30, 2023].
Horvath, S., Raj, K. DNA methylation-based biomarkers and the epigenetic clock theory of ageing. Nat Rev Genet vol. 19, Jun. 2018 (published Apr. 11, 2018) 19, pp. 371-384, [https://doi.org/10.1038/s41576-018-0004-3].
Chen et al., DNA methylation-based measures of biological age: meta-analysis predicting time to death, Aging, vol. 8, No. 9. Sep. 28, 2016, pp. 1844-1865 [ https://doi.org/10.18632/aging.101020].
Weidner et al ,Aging of blood can be tracked by DNA methylation changes at just three CpG sites, Genome Biology 15:R24, Feb. 3, 2014, 11 pages. [http://genomebiology.com/2014/15/2/R2].
"Our Story—Pioneering technologies aimed at extending human healthspan", OneSkin, Apr. 2023, 8 pages (accessed Apr. 17, 2023 https://www.oneskin.co/pages/our-story).
Castelli et al. HDL cholesterol and other lipids in coronary heart disease. National Institutes of Health, National Heart, Lung, and Blood Institute, Heart Disease Epidemiology Study, Circulation, vol. 55, pp. 767-772.
Li et al, Novel feature selection methods for construction of accurate epigenetic clocks, PLOS Computational Biology, Aug. 19, 2022, 18 pages [https://doi.org/10.1371/journal.pcbi.1009938].
Belsky et al., "Quantification of the pace of biological aging in humans through a blood test, the DunedinPoAm DNA methylation algorithm." eLife, 9:e54870, May 5, 2020, 35 pages.
Illumina, "Infinium HumanMethylation450 v1.2 BeadChip Product Files", accessed at «https://support.illumina.com/downloads/humanmethylation450_15017482_v1_2_product_files.html», 2013.

* cited by examiner

*Primary Examiner* — Samuel C Woolwine
*Assistant Examiner* — Carolyn L Greene
(74) *Attorney, Agent, or Firm* — HAYNES BEFFEL & WOLFELD, LLP; Ernest J. Beffel, Jr.

(57) ABSTRACT

We propose a method of generating an epigenetic age prediction. The method includes providing a sample extraction test kit, and receiving a sample extracted by the sample extraction test kit. The method further includes extracting DNA from the sample and processing the DNA to receive processed DNA. The method further includes amplifying a plurality of loci in the processed DNA to receive amplified DNA and processing the amplified DNA to receive a plurality of methylation values for one or more CpG sites in the plurality of loci.

9 Claims, 11 Drawing Sheets

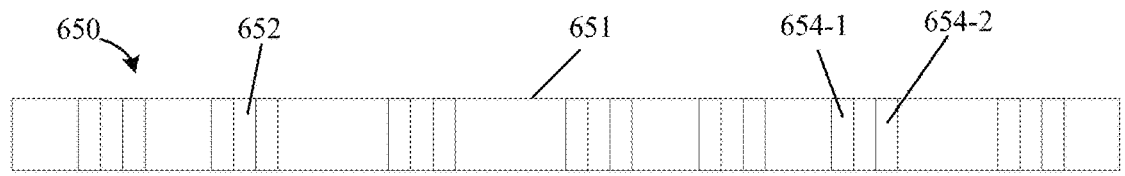
FIG. 6A
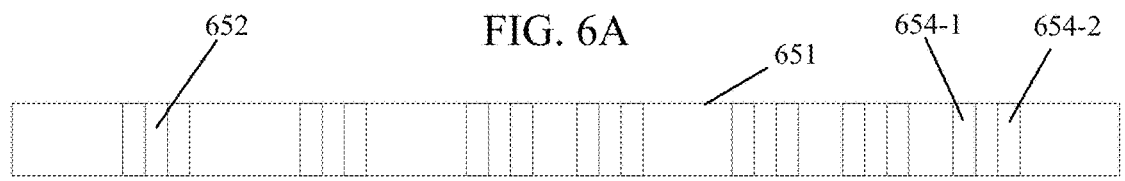
FIG. 6B
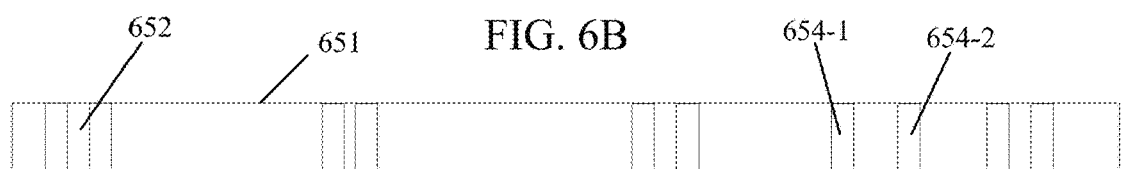
FIG. 6C
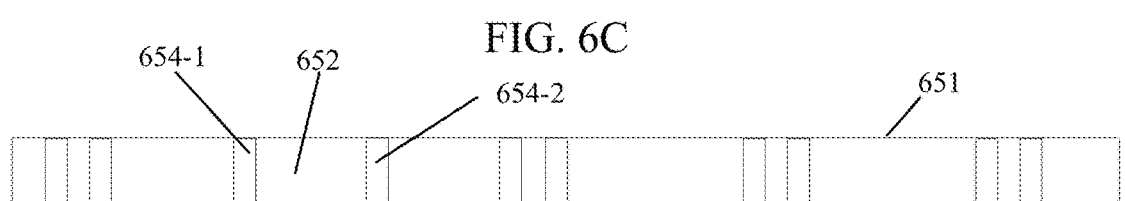
FIG. 6D
FIG. 6E
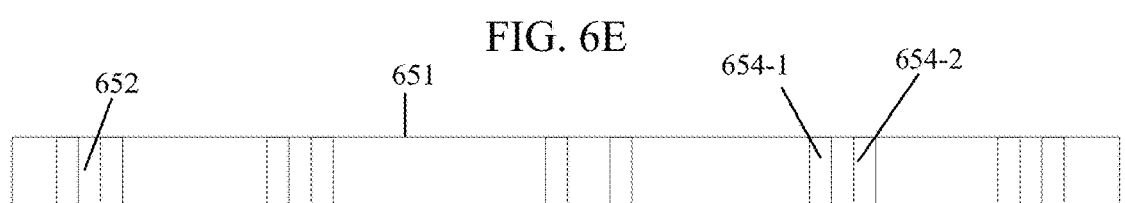
FIG. 6F
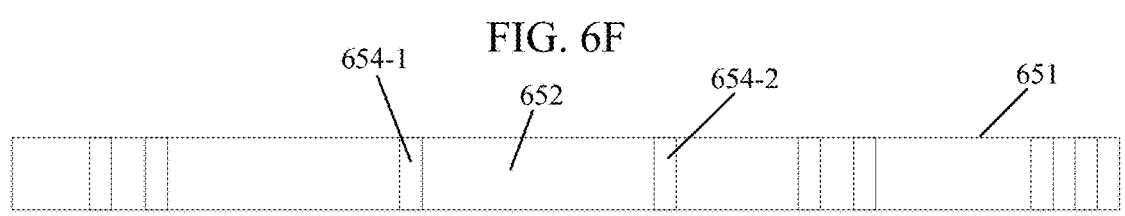
FIG. 6G
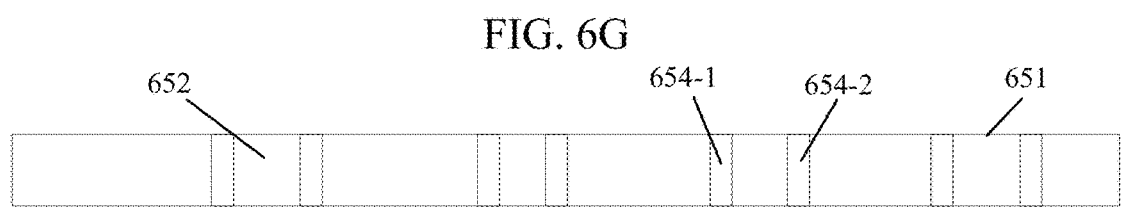
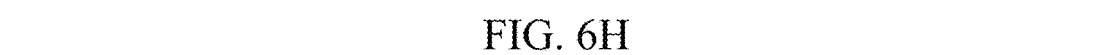
FIG. 6H

PCR-BASED EPIGENETIC AGE PREDICTION

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Genomics, in the broad sense, also referred to as functional genomics, aims to characterize the function of every genomic element of an organism by using genome-scale assays such as genome sequencing, transcriptome profiling and proteomics. Genomics arose as a data driven science, and operates by discovering novel properties from explorations of genome-scale data rather than by testing preconceived models and hypotheses. Applications of genomics include finding associations between genotype and phenotype, discovering biomarkers for patient stratification, predicting the function of genes, and charting biochemically active genomic regions such as transcriptional enhancers.

Genomics data are too large and too complex to be mined solely by visual investigation of pairwise correlations. Instead, analytical tools are required to support the discovery of unanticipated relationships, to derive novel hypotheses and models and to make predictions. Unlike some algorithms, in which assumptions and domain expertise are hard coded, machine learning algorithms are designed to automatically detect patterns in data. Hence, machine learning algorithms are suited to data-driven sciences and, in particular, to genomics. However, the performance of machine learning algorithms can strongly depend on how the data are represented, that is, on how each variable (also called a feature) is computed. For instance, to classify a tumor as malign or benign from a fluorescent microscopy image, a preprocessing algorithm could detect cells, identify the cell type, and generate a list of cell counts for each cell type.

A machine learning model can take the estimated cell counts, which are examples of handcrafted features, as input features to classify the tumor. A central issue is that classification performance depends heavily on the quality and the relevance of these features. For example, relevant visual features such as cell morphology, distances between cells or localization within an organ are not captured in cell counts, and this incomplete representation of the data may reduce classification accuracy.

Deep learning, a subdiscipline of machine learning, addresses this issue by embedding the computation of features into the machine learning model itself to yield end-to-end models. This outcome has been realized through the development of deep neural networks, machine learning models that comprise successive elementary operations, which compute increasingly more complex features by taking the results of preceding operations as input. Deep neural networks are able to improve prediction accuracy by discovering relevant features of high complexity, such as the cell morphology and spatial organization of cells in the above example. The construction and training of deep neural networks have been enabled by the explosion of data, algorithmic advances, and substantial increases in computational capacity, particularly through the use of graphical processing units (GPUs).

The goal of supervised learning is to obtain a model that takes features as input and returns a prediction for a so-called target variable. An example of a supervised learning problem is one that predicts whether an intron is spliced out or not (the target) given features on the RNA such as the presence or absence of the canonical splice site sequence, the location of the splicing branchpoint or intron length. Training a machine learning model refers to learning its parameters, which commonly involves minimizing a loss function on training data with the aim of making accurate predictions on unseen data.

For many supervised learning problems in computational biology, the input data can be represented as a table with multiple columns, or features, each of which contains numerical or categorical data that are potentially useful for making predictions. Some input data are naturally represented as features in a table (such as temperature or time), whereas other input data need to be first transformed (such as deoxyribonucleic acid (DNA) sequence into k-mer counts) using a process called feature extraction to fit a tabular representation. For the intron-splicing prediction problem, the presence or absence of the canonical splice site sequence, the location of the splicing branchpoint and the intron length can be preprocessed features collected in a tabular format. Tabular data are standard for a wide range of supervised machine learning models, ranging from simple linear models, such as logistic regression, to more flexible nonlinear models, such as neural networks and many others.

Logistic regression is a binary classifier, that is, a supervised learning model that predicts a binary target variable. Specifically, logistic regression predicts the probability of the positive class by computing a weighted sum of the input features mapped to the [0, 1] interval using the sigmoid function, a type of activation function. The parameters of logistic regression, or other linear classifiers that use different activation functions, are the weights in the weighted sum. Linear classifiers fail when the classes, for instance, that of an intron spliced out or not, cannot be well discriminated with a weighted sum of input features. To improve predictive performance, new input features can be manually added by transforming or combining existing features in new ways, for example, by taking powers or pairwise products.

Neural networks use hidden layers to learn these nonlinear feature transformations automatically. Each hidden layer can be thought of as multiple linear models with their output transformed by a nonlinear activation function, such as the sigmoid function or the more popular rectified-linear unit (ReLU). Together, these layers compose the input features into relevant complex patterns, which facilitates the task of distinguishing two classes.

Deep neural networks use many hidden layers, and a layer is said to be fully-connected when each neuron receives inputs from all neurons of the preceding layer. Neural networks are commonly trained using stochastic gradient descent, an algorithm suited to training models on very large data sets. Implementation of neural networks using modern deep learning frameworks enables rapid prototyping with different architectures and data sets. Fully-connected neural networks can be used for a number of genomics applications, which include predicting the percentage of exons spliced in for a given sequence from sequence features such as the presence of binding motifs of splice factors or sequence conservation; prioritizing potential disease-causing genetic variants; and predicting cis-regulatory elements in a given genomic region using features such as chromatin marks, gene expression and evolutionary conservation.

Local dependencies in spatial and longitudinal data must be considered for effective predictions. For example, shuffling a DNA sequence or the pixels of an image severely disrupts informative patterns. These local dependencies set spatial or longitudinal data apart from tabular data, for which the ordering of the features is arbitrary. Consider the problem of classifying genomic regions as bound versus unbound by a particular transcription factor, in which bound regions are defined as high-confidence binding events in chromatin immunoprecipitation following by sequencing (ChIP-seq) data. Transcription factors bind to DNA by recognizing sequence motifs. A fully-connected layer based on sequence-derived features, such as the number of k-mer instances or the position weight matrix (PWM) matches in the sequence, can be used for this task. As k-mer or PWM instance frequencies are robust to shifting motifs within the sequence, such models could generalize well to sequences with the same motifs located at different positions. However, they would fail to recognize patterns in which transcription factor binding depends on a combination of multiple motifs with well-defined spacing. Furthermore, the number of possible kmers increases exponentially with k-mer length, which poses both storage and overfitting challenges.

A convolutional layer is a special form of fully-connected layer in which the same fully-connected layer is applied locally, for example, in a 6 bp window, to all sequence positions. This approach can also be viewed as scanning the sequence using multiple PWMs, for example, for transcription factors GATAI and TAL I. By using the same model parameters across positions, the total number of parameters is drastically reduced, and the network is able to detect a motif at positions not seen during training. Each convolutional layer scans the sequence with several filters by producing a scalar value at every position, which quantifies the match between the filter and the sequence. As in fully-connected neural networks, a nonlinear activation function (commonly ReLU) is applied at each layer. Next, a pooling operation is applied, which aggregates the activations in contiguous bins across the positional axis, commonly taking the maximal or average activation for each channel. Pooling reduces the effective sequence length and coarsens the signal. The subsequent convolutional layer composes the output of the previous layer and is able to detect whether a GATAI motif and TALI motif were present at some distance range. Finally, the output of the convolutional layers can be used as input to a fully-connected neural network to perform the final prediction task. Hence, different types of neural network layers (e.g., fully-connected layers and convolutional layers) can be combined within a single neural network.

Convolutional neural networks (CNNs) can predict various molecular phenotypes on the basis of DNA sequence alone. Applications include classifying transcription factor binding sites and predicting molecular phenotypes such as chromatin features, DNA contact maps, DNA methylation, gene expression, translation efficiency, RBP binding, and microRNA (miRNA) targets. In addition to predicting molecular phenotypes from the sequence, convolutional neural networks can be applied to more technical tasks traditionally addressed by handcrafted bioinformatics pipelines. For example, convolutional neural networks can predict the specificity of guide RNA, denoise ChIP-seq, enhance Hi-C data resolution, predict the laboratory of origin from DNA sequences and call genetic variants. Convolutional neural networks have also been employed to model long-range dependencies in the genome. Although interacting regulatory elements may be distantly located on the unfolded linear DNA sequence, these elements are often proximal in the actual 3D chromatin conformation. Hence, modelling molecular phenotypes from the linear DNA sequence, albeit a crude approximation of the chromatin, can be improved by allowing for long-range dependencies and allowing the model to implicitly learn aspects of the 3D organization, such as promoter-enhancer looping. This is achieved by using dilated convolutions, which have a receptive field of up to 32 kb. Dilated convolutions also allow splice sites to be predicted from sequence using a receptive field of 10 kb, thereby enabling the integration of genetic sequence across distances as long as typical human introns (See Jaganathan, K. et al. Predicting splicing from primary sequence with deep learning. Cell 176, 535-548 (2019)).

Different types of neural network can be characterized by their parameter-sharing schemes. For example, fully-connected layers have no parameter sharing, whereas convolutional layers impose translational invariance by applying the same filters at every position of their input. Recurrent neural networks (RNNs) are an alternative to convolutional neural networks for processing sequential data, such as DNA sequences or time series, that implement a different parameter-sharing scheme. Recurrent neural networks apply the same operation to each sequence element. The operation takes as input the memory of the previous sequence element and the new input. It updates the memory and optionally emits an output, which is either passed on to subsequent layers or is directly used as model predictions. By applying the same model at each sequence element, recurrent neural networks are invariant to the position index in the processed sequence. For example, a recurrent neural network can detect an open reading frame in a DNA sequence regardless of the position in the sequence. This task requires the recognition of a certain series of inputs, such as the start codon followed by an in-frame stop codon.

The main advantage of recurrent neural networks over convolutional neural networks is that they are, in theory, able to carry over information through infinitely long sequences via memory. Furthermore, recurrent neural networks can naturally process sequences of widely varying length, such as mRNA sequences. However, convolutional neural networks combined with various tricks (such as dilated convolutions) can reach comparable or even better performances than recurrent neural networks on sequence-modelling tasks, such as audio synthesis and machine translation. Recurrent neural networks can aggregate the outputs of convolutional neural networks for predicting single-cell DNA methylation states, RBP binding, transcription factor binding, and DNA accessibility. Moreover, because recurrent neural networks apply a sequential operation, they cannot be easily parallelized and are hence much slower to compute than convolutional neural networks.

Each human has a unique genetic code, though a large portion of the human genetic code is common for all humans. In some cases, a human genetic code may include an outlier, called a genetic variant, that may be common among individuals of a relatively small group of the human population. For example, a particular human protein may comprise a specific sequence of amino acids, whereas a variant of that protein may differ by one amino acid in the otherwise same specific sequence.

Genetic variants may be pathogenetic, leading to diseases. Though most of such genetic variants have been depleted from genomes by natural selection, an ability to identify which genetic variants are likely to be pathogenic can help researchers focus on these genetic variants to gain an understanding of the corresponding diseases and their diagnostics, treatments, or cures. The clinical interpretation of millions of human genetic variants remains unclear. Some of the most frequent pathogenic variants are single nucleotide missense mutations that change the amino acid of a protein. However, not all missense mutations are pathogenic.

Models that can predict molecular phenotypes directly from biological sequences can be used as in silico perturbation tools to probe the associations between genetic variation and phenotypic variation and have emerged as new methods for quantitative trait loci identification and variant prioritization. These approaches are of major importance given that the majority of variants identified by genome-wide association studies of complex phenotypes are non-coding, which makes it challenging to estimate their effects and contribution to phenotypes. Moreover, linkage disequilibrium results in blocks of variants being co-inherited, which creates difficulties in pinpointing individual causal variants. Thus, sequence-based deep learning models that can be used as interrogation tools for assessing the impact of such variants offer a promising approach to find potential drivers of complex phenotypes. One example includes predicting the effect of noncoding single-nucleotide variants and short insertions or deletions (indels) indirectly from the difference between two variants in terms of transcription factor binding, chromatin accessibility or gene expression predictions. Another example includes predicting novel splice site creation from sequence or quantitative effects of genetic variants on splicing.

Human health and age can be measured in a variety of different ways. A human's chronological age, that is a time that an individual is alive, is one form of measure of a human's health and age. Another form of measuring a human's age is a subjective biological age that is used to account for a shortfall between a population average life expectancy and the perceived life expectancy of an individual of the same age. A human's environment or behavior can cause their body to biologically age at an accelerated rate. It has been difficult in the past to estimate an individual's biological age with accuracy. Additionally, when an individual's biological age can be estimated, the process to do so is typically accompanied with a high financial cost.

INCORPORATION

This application incorporates by reference U.S. patent application Ser. No. 17/525,552, filed Nov. 12, 2021.

SUMMARY

We propose a method of generating an epigenetic age prediction. The method includes providing a sample extraction test kit, and receiving a sample extracted by the sample extraction test kit. The method further includes extracting DNA from the sample and processing the DNA to receive processed DNA. The method further includes amplifying a plurality of loci in the processed DNA to receive amplified DNA and processing the amplified DNA to receive a plurality of methylation values for one or more CpG sites in the plurality of loci.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

FIGS. 6A-6H illustrate diagrams showing example amplifications of portions of DNA.

DETAILED DESCRIPTION

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Many studies have shown that a human's environment or behavior can cause their body to biologically age at an accelerated rate. It has been difficult in the past to estimate an individual's biological age with accuracy. Additionally, the methods of estimating an individual's biological age that have been proven to be accurate are typically accompanied with a high financial cost to process. Genetics have been used with limited effectiveness as aging does not predictively correlate with alterations of the human DNA sequence. Epigenetics, however, have been shown to correlate with biological aging.

Epigenetics is the study of changes in gene expression that are not the result of changes in the DNA sequence itself. Some examples of processes that are in the field of epigenetics include acetylation, phosphorylation, ubiquitylation, and methylation. Methylation specifically, as we have found can correlate with a number of different diseases, conditions, the health of an individual as well as the biological age of the individual. Methylation can occur at several million different places in the human genome. Methylation can also differ from tissue to tissue and even cell to cell in the human body.

Figure 1:
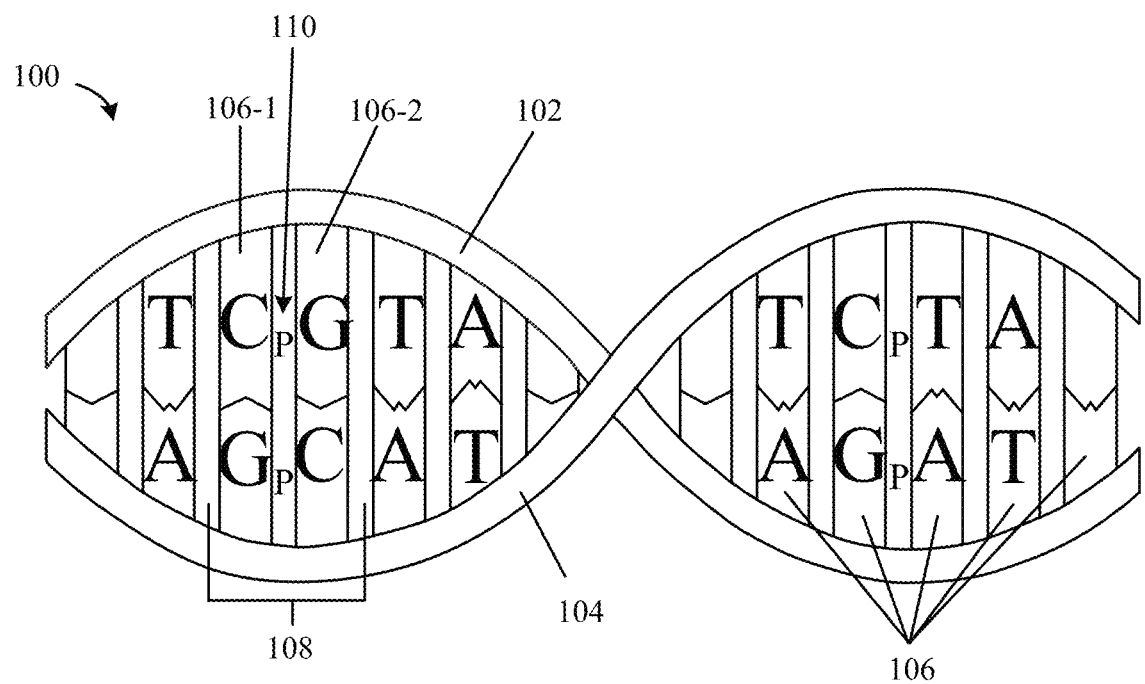
FIG. 1 illustrates a diagram showing an example portion of DNA.

FIG. 1 is a diagram showing an example portion 100 of DNA. Portion 100 includes strand 102 and strand 104. Nucleotide base pairs 106 extend along the length of strands 102 and 104. An area where a cytosine nucleotide 106-1 is followed by a guanine nucleotide 106-2 is called a CpG site 108. CpG sites 108 are also defined in that only one phosphate group 110 separates the cytosine and guanine nucleotide base pairs 106.

Figure 2:
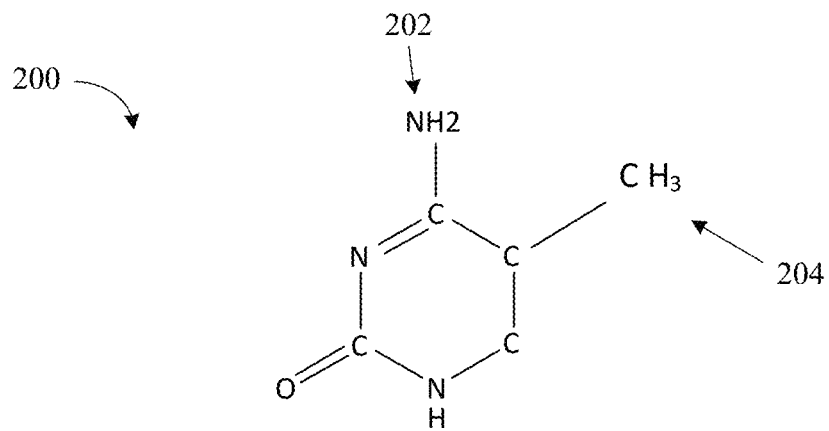
FIG. 2 illustrates a molecular structure diagram showing an example methylated cytosine molecule.

FIG. 2 is a molecular structure diagram showing an example 5-Methylcytosine molecule 200. 5-Methylcytosine is an example of a methylated form of cytosine. Molecule 200 includes a cytosine portion 202 and a methyl group portion 204. As shown, the methyl group portion 204 is attached to the 5th atom in the 6-atom ring, counting counterclockwise from the NH-bonded nitrogen at the six o'clock position of the cytosine portion 202.

Figure 3:
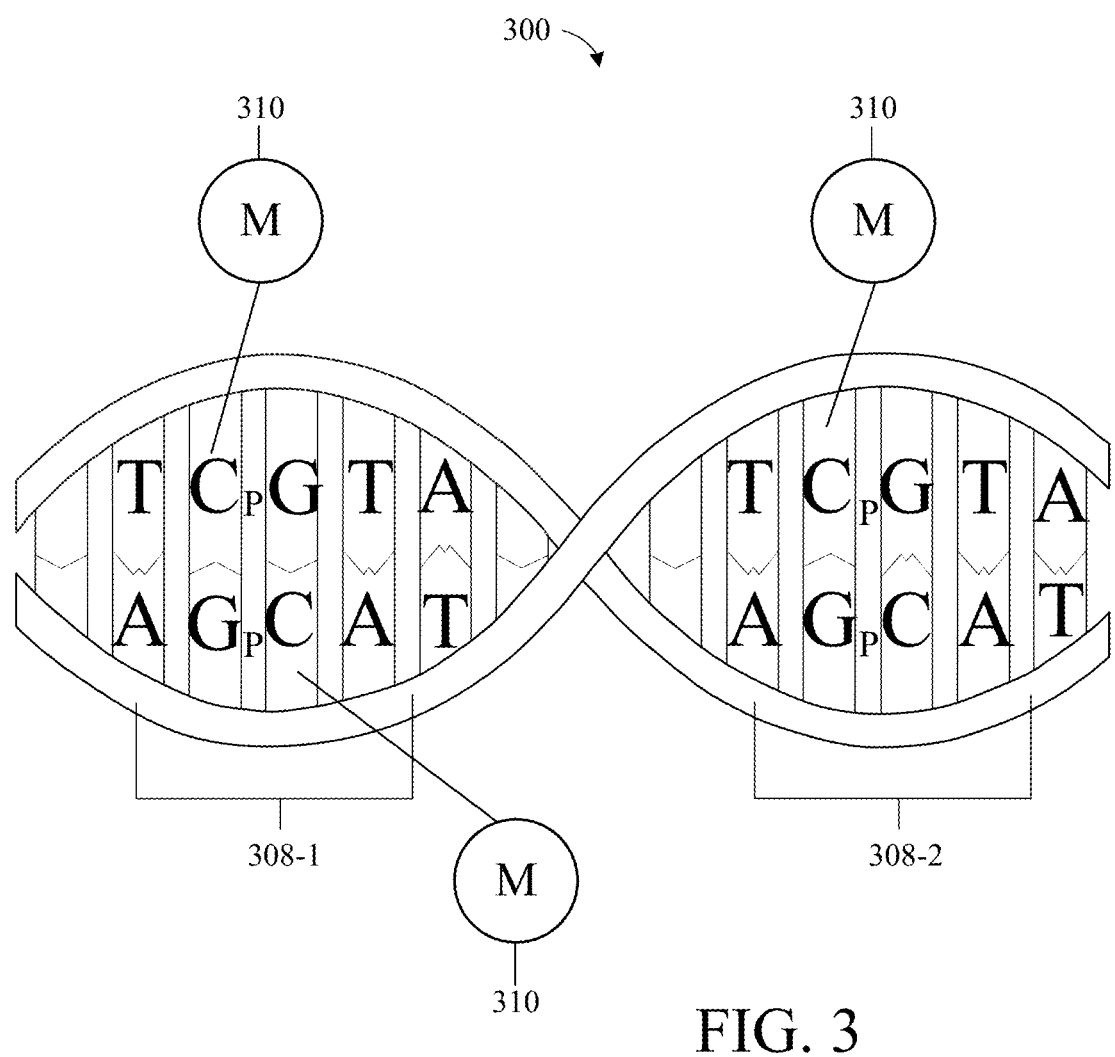
FIG. 3 illustrates a diagram showing an example portion of methylated DNA.

FIG. 3 is a diagram showing an example portion 300 of methylated DNA. Portion 300 includes two CpG sites 308-1 and 308-2 (collectively referred to as CpG sites 308). The first CpG site 308-1 has two methyl groups 310 attached to the two cytosine molecules. This configuration of CpG site 308-1 is called being fully methylated. The second CpG site 308-2 has a single methyl group 310 attached to one of the two cytosine molecules. This configuration of CpG site 308-2 is called being hemi-methylated. When there are no methyl groups attached to either cytosine, then the CpG site is considered to be unmethylated.

Figure 4A:
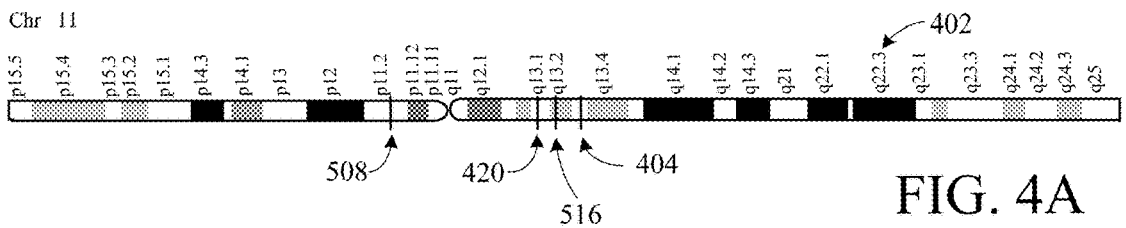
FIG. 4A-4N illustrate diagrams showing genomic diagrams of chromosomes.
Figure 4B:
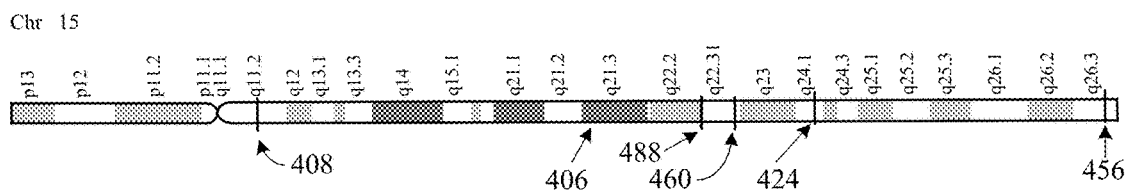
Figure 4C:
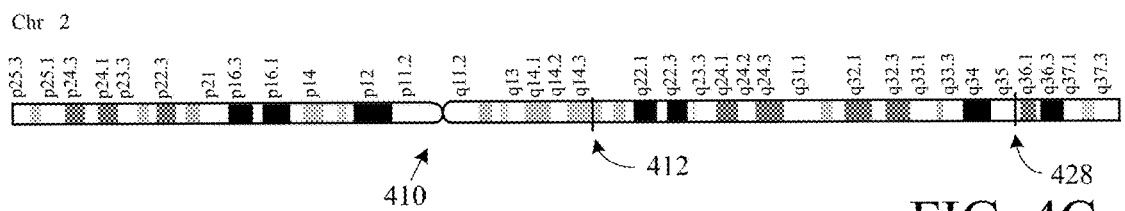
Figure 4D:
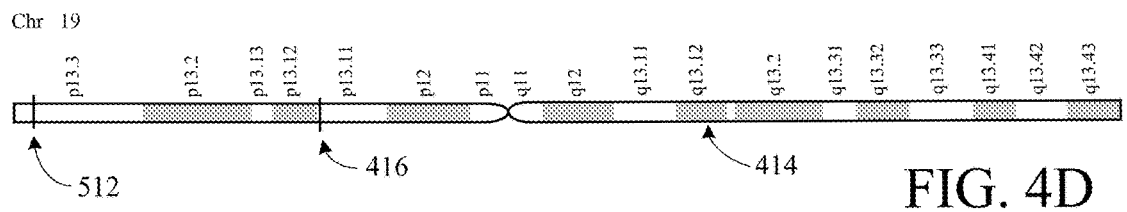
Figure 4E:
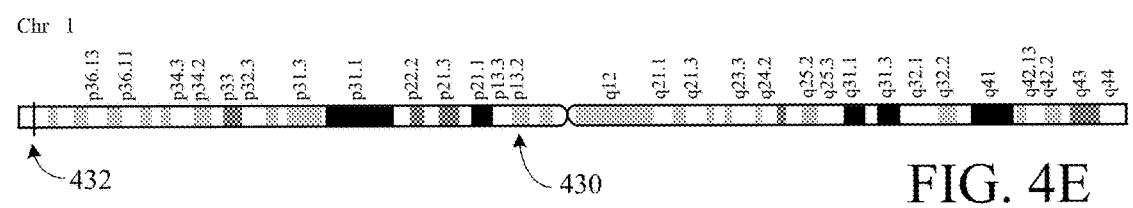
Figure 4F:
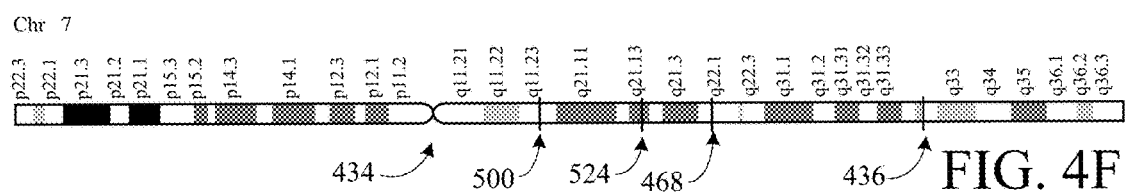
Figure 4G:
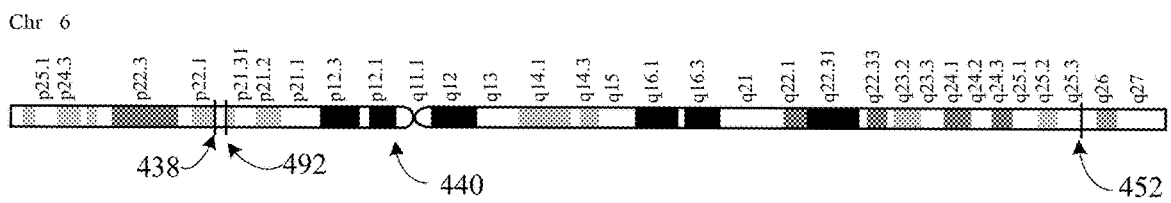
Figure 4H:
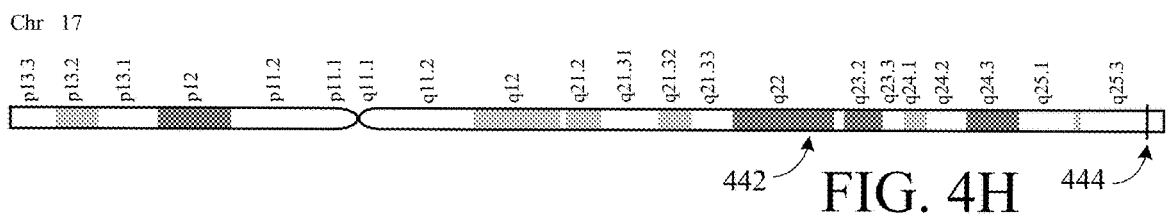
Figure 4I:
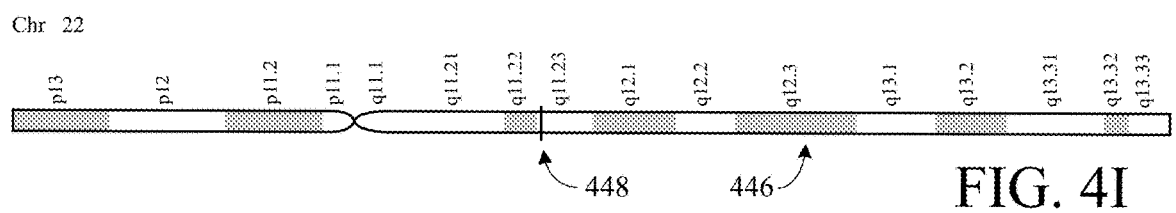
Figure 4J:
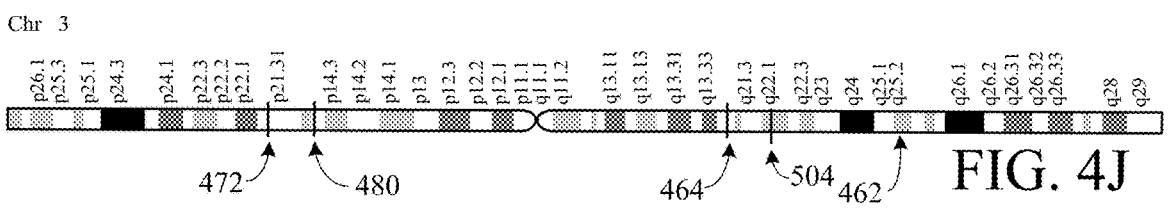
Figure 4K:
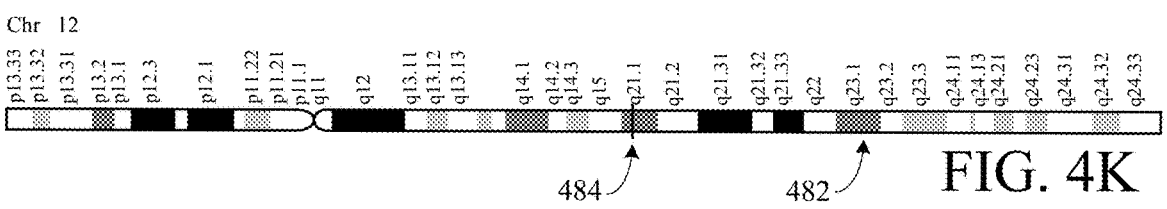
Figure 4L:
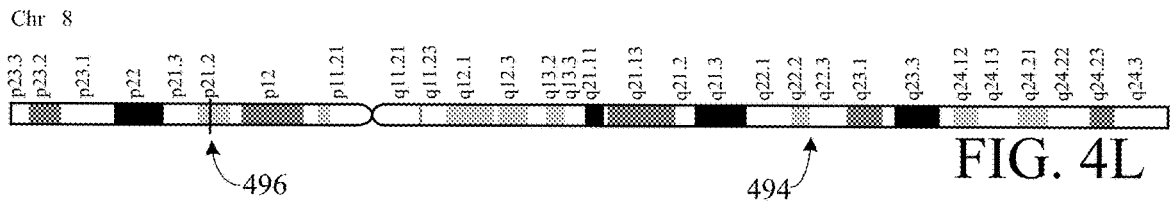
Figure 4M:
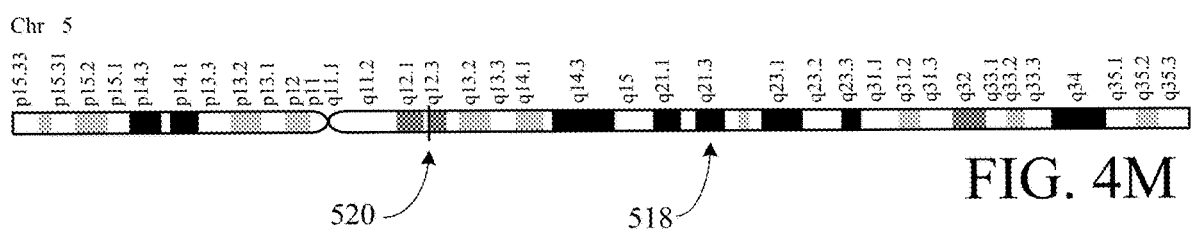
Figure 4N:
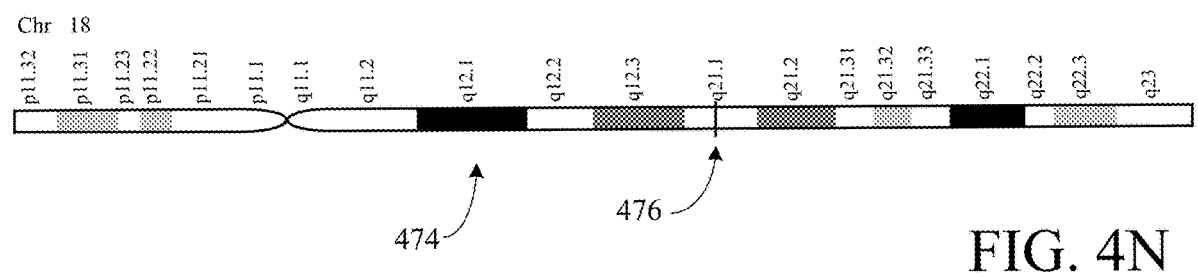

FIG. 4A-4N illustrate genomic diagrams of chromosomes. Epigenetics, by definition, can alter the way in which a gene behaves based on non-sequence changing factors like methylation. If key aging gene behaviors are modified by methylation, then the methylation status of CpG sites in these genes may provide insight on the biological age of an individual.

FIG. 4A illustrates a genomic diagram 402 of chromosome 11. At location 404 is the Fibroblast growth Factor 19 (FGF19) gene. FGF family members possess broad mitogenic and cell survival activities and are involved in a variety of biological processes, including embryonic development cell growth, morphogenesis, tissue repair, tumor growth and invasion. The FGF19 protein is produced in the gut where it functions as a hormone, regulating bile acid synthesis, with effects on glucose, cholesterol, and lipid metabolism. Reduced synthesis, and blood levels, has been linked to chronic bile acid diarrhea and as well as certain metabolic diseases. FGF19 may be used in treatment of metabolic disease. FGF19 plays a role in maintaining health and metabolic homeostasis. High levels of circulating FGF19 increases energy spending and reduces fat tissue. FGF 19 can have hypertrophic effect on skeletal muscle. FGF 19, therefore, appears be a therapeutic target to limit aging-associated muscle loss and other diseases characterized by muscle atrophy (obesity, cancer, kidney failure). The CpG site, Cg27330757, is a probe mapping to protein coding Fibroblast growth Factor 19 (FGFl 9) gene.

At location 420 is the Mono-ADP Ribosylhydrolase 1 (MACRODI) gene. The protein encoded by this gene has a mono-ADP-ribose hydrolase enzymatic activity, i.e. removing ADPribose in proteins bearing a single ADP-ribose moiety, and is thus involved in the finetuning of ADP-ribosylation systems. ADP-ribosylation is a (reversible) post-translational protein modification controlling major cellular and biological processes, including DNA damage repair, cell proliferation and differentiation, metabolism, stress, and immune responses. MACRODI appears to primarily be a mitochondrial protein and is highly expressed in skeletal muscle (a tissue with high mitochondrial content). It has been shown to play a role estrogen and androgen signaling and sirtuin activity. Dysregulation of MACRODI has been associated with familial hypercholesterolemia and pathogenesis of several forms of cancer, and particular with progression of hormone-dependent cancers. The CpG site, cg15769472, is a probe mapping to the protein coding MACRODI gene.

At location 508 is the Diacylglycerol Kinase Zeta (DGKZ) gene. The DGKZ gene coding for the diacylglycerol kinase zeta. This kinase transforms diacylglycerol (DAG) into phosphatidic acid (PA). The latter product activates mammalian target of rapamycin complex I or mechanistic target of rapamycin complex I (m TORC 1). The overall effect of mTORCl activation is upregulation of anabolic pathways. Downregulation of m TORC I has been shown to drastically increase lifespan. The CpG site, cg00530720, is a probe mapping to the promoter of the DGKZ gene.

At position 516 is the CD248 Molecule (CD248) gene. The cpG site, cg06419846, is a probe mapping to the CD248 gene.

FIG. 4B illustrates a genomic diagram 406 of chromosome 15. At location 408 is the WAS Protein Homolog Associated with Actin, Golgi Membranes and Microtubules Pseudogene 3 (WHAMMP3) gene. This pseudogene has been associated with Prader-Willi syndrome, a severe developmental disorder. This syndrome is caused by epigenetics defect on chromosome 15. More specifically the absence of paternally expressed imprinted genes at I Sal I 0.2-q 13, paternal deletions of this region, maternal uniparental dysomy of chromosome 15 or an imprinting defect. Multiple imprinted genes in this region contribute to the complete phenotype of Prader-Willi. The CpG site, cg04777312, is a probe mapping to the pseudogene WHAMMP3.

At location 424 is the PML gene. The phosphoprotein coded by this gene localizes to nuclear bodies where it functions as a transcription factor and tumor suppressor. Expression is cellcycle related and it regulates the p53 response to oncogenic signals. The gene is often involved in the PML-RARA translocation between chromosomes 15 and 17, a key event in acute promyelocytic leukemia (APL). The exact role of PML-nuclear body (PML-NBs) interaction is still under further investigation. Current consensus is that PML-NBs are structures which are involved in processing cell damages and DNA-double strand break repairs. Interestingly, these PML-NBs bodies have been shown to decrease with age and their stress response also declines with age. The latter can be in a p53 dependent or independent way. PIVIL has also been implicated in cellular senescence, particularly its induction and acts as a modulator of the Werner syndrome, a type of progeria. The CpG site, cg05697231, is a probe mapping to the south shore of a CpG island in the PML gene.

At location 456 is the ADAM Metallopeptidase with Thrombospondin Type I Motif 17 (ADAMTS 17) gene. The CpG site, cg07394446, is a probe mapping to ADAMTS17.

At location 460 is the SMAD Family Member 6 (SMAD6) gene. The CpG site, cg07124372, is a probe mapping to SMAD6.

At location 488 is the Carbonic Anhydrase 12 (CAI 2) gene. The CpG site, cg10091775, is a probe mapping to CAI 2.

FIG. 4C illustrates a genomic diagram 410 of chromosome 2. At location 412 is the Bridging Integrator I (BIN 1) gene. The BIN I gene provides instructions for making a protein that is found in tissues throughout the body, where it interacts with a variety of other proteins. The BIN I protein is involved in endocytosis as well as apoptosis, inflammation, and calcium homeostasis. The BIN I protein may act as a tumor suppressor protein, preventing cells from growing and dividing too rapidly or in an uncontrolled way. In addition to its roles in tumor suppression and muscle development, multiple GWAS studies identified BIN I as risk factor for late-onset Alzheimer's disease. While the exact pathogenic mechanism of BIN I is still unknown, both high-risk variants and DNA methylation have been suggested as mechanisms affecting BIN I transcription and Alzheimer's Disease risk. The CpG site, cg27405400, is a probe mapping to the BIN] gene.

At location 428 is the Protein Tyrosine Phosphatase Receptor Type N (PTPRN) gene. This gene codes for a protein receptor involved in a multitude of processes including cell growth, differentiation, mitotic cycle, and oncogenic transformation. More specifically, this PTPRN plays a significant role in the signal transduction of multiple hormone pathways (neurotransmitters, insulin and pituitary hormones). PTPRN expression levels are also used as a prognostic tool for hepatocellular carcinoma (negative outcome correlation). The CpG site, cg03545227, is a probe mapping in the protein tyrosine phosphatase receptor type N (PTPRN) gene.

FIG. 4D illustrates a genomic diagram 414 of chromosome 19. At location 416 is the Kruppel-Like Factor 2 (KLF2) gene. This gene encodes for a transcription factor (zinc finger protein) found in many different cell types. Expression starts early in mammalian development and plays a role in processes ranging from adipogenesis, embryonic erythropoiesis, epithelial integrity, inflammation, and t-cell viability. Its role in inflammation is of specific interest as chronic systemic inflammation highly correlates with aging and age associated disease. The downstream effect of KLF2 expression is the downregulation of inflammation and reduction of pro-inflammatory activity of nuclear factor kappa beta (NF-kB). In humans with chronic infections and inflammatory disease such as sepsis, rheumatoid arthritis, atherosclerosis a reduction of 30 to 50% in KLF2 levels has been observed. The CpG site, cg26842024, is a probe mapping to a CpG island in the Kruppel-Like Factor 2 (KLF2) gene.

At location 512 is the Midnolin (MIDN) gene. The cpG site, cg07843568 is a probe mapping to MIDN.

FIG. 4E illustrates a genomic diagram 430 of chromosome 1. At location 432 is the Multiple EGF Like Domains 6 (MEGF6) gene. This gene plays a role in cell adhesion, motility and proliferation and is also involved in apoptotic cell phagocytosis. Mutations in this gene are associated with a predisposition to osteoporosis. The CpG site, cg23686029, is a probe mapping in the MEGF6 gene.

FIG. 4F illustrates a genomic diagram 434 of chromosome 7. At location 436 is the Kruppel-Like Factor 14 (KLF 14) gene. This gene encodes a member of the Kruppel-like family of transcription factors and shows maternal monoallelic expression in a wide variety of tissues. The encoded protein functions as a transcriptional co-repressor and is induced by transforming growth factor-beta (TGF-beta) to repress TGF-beta receptor Il gene expression. This gene exhibits imprinted expression from the maternal allele in embryonic and extra-embryonic tissues. Variations near this transcription factor are highly associated with coronary artery disease. The CpG site, cg08097417, is a probe mapping to the KLF14 gene.

At location 468 is the Stromal Antigen 3 (STAG3/GPC2) gene. The cpG site, cg18691434, is a probe mapping to the STAG3/GPC2 gene. At location 500 is the Huntingtin Interacting Protein I (HIPI) gene. The cpG site, cg13702357, is a probe mapping to the HIPI gene. At location 524 is the DPY19L2 Pseudogene 4 (DPY19L2P4) gene. The cpG site, cg22370005, is a probe mapping to the DPYI 9L2P4 gene.

FIG. 4G illustrates a genomic diagram 438 of chromosome 6. At location 440 is the Protein Phosphatase I Regulatory Subunit 18 (PPP IRI 8) gene. The protein that is encoded by this gene, phosphatase-1 (PPI), plays a role in glucose metabolism in the liver by controlling the activity of phosphorylase a that breaks down glycogen to release glucose in the blood stream. Furthermore, PPI is also involved in diverse, essential cellular processes such as cell cycle progression, protein synthesis, muscle contraction, carbohydrate metabolism, transcription and neuronal signaling. In Alzheimer's disease, expression of PPI is significantly reduced in both white and grey matter. The CpG site, cg23197007, is a probe that maps to the S-shore of the PPPIR18 gene.

At location 452 is the TMEM181 gene. The CpG site, cg02447229, is a probe mapping to the TMEM181 gene. At location 492 is the Zinc Finger and BTB Domain Containing 12 (ZBTB 12) gene. The cpG site, cg06540876, is a probe mapping to the ZBTB 12 gene.

FIG. 4H illustrates a genomic diagram 442 of chromosome 17. At location 444 is the dicarbonyl and L-xylulose reductase (DCXR) gene. One of its functions is to perform a chemical reaction that converts a sugar called L-xylulose to a molecule called xylitol. This reaction is one step in a process by which the body can use sugars for energy. There are two versions of L-xylulose reductase in the body, known as the major isoform and the minor isoform. The DCXR gene provides instructions for making the major isoform, which converts L-xylulose more efficiently than the minor isoform. It is unclear if the minor isoform is produced from the DCXR gene or another gene. Another function of the DCXR protein is to break down toxic compounds called alpha-dicarbonyl compounds. The DCXR protein is also one of several proteins that get attached to the surface of sperm cells as they mature. DCXR is involved in the interaction of a sperm cell with an egg cell during fertilization. The CpG site, cg07073120, is a probe that maps to the promotor region of the DCXR gene.

FIG. 4I illustrates a genomic diagram 446 of chromosome 22. At location 448 is the BCR Activator of RhoGEF and GTPase (BCR) gene. The cpG site, cg04028010, is a probe mapping to the BCR gene.

FIG. 4J illustrates a genomic diagram 462 of chromosome 3. At location 464 is the Myosin Light Chain Kinase (MYLK) gene. This gene codes for a myosin light chain kinase (MLCK), which is a calcium/calmodulin dependent enzyme active in smooth muscle tissue (involuntary muscle). It phosphorylates myosin light chains to facilitate their interaction with actin to produce muscle contraction. A second function of the MLCK protein is regulation of the epithelial tight junction. These are the gaps between the epithelial cells and their size is of major biological importance as this determines the selective permeability of the epithelial barrier. This selectivity allows absorption and secretion of nutrients and metabolites while protecting the sterile tissues against pathogens. A secondary promotor drives the expression of a second gene transcript: telokin. This small protein is identical to the c-terminus of the Myosin Light Chain Kinase (MYLK) protein and helps stabilize unphosphorylated myosin filaments. Abnormal expression of MYLK have been observed in many inflammatory diseases such as, pancreatitis, asthma, inflammatory bowel disease.

At location 472 is the Transglutaminase 4 (TGM4) gene. The CpG site, cg12112234, is a probe mapping to the TGM4 gene.

At location 480 is the Scm Like With Four Mbt Domains 1 (SFMBTI) gene. The cpG site, cg03607117, is a probe mapping to the SFMBTI gene.

At location 504 is Nudix Hydrolase 16 (NUDT16P) gene. The cpG site, cg22575379, is a probe mapping to the NUDT16P gene.

FIG. 4K illustrates a genomic diagram 482 of chromosome 12. At location 484 is the Thyrotropin Releasing Hormone Degrading Enzyme (LOC283392/TRHDE) gene. The cpG site, cg13663218, is a probe mapping to the LOC283392/TRHDE gene.

FIG. 4L illustrates a genomic diagram 496 of chromosome 8. At location 494 is the Neurofilament Medium Chain (NEFM) gene. The CpG site, cg07502389, is a probe mapping to the NEFM gene.

FIG. 4M illustrates a genomic diagram 518 of chromosome 5. At location 520 is the Ring Finger Protein 180 (RNF180) gene. The RNF180 gene codes for RING-Type E3 Ubiquitin Transferase. RING-type E3s are implicated as tumor suppressors, oncogenes, and mediators of endocytosis, and play critical roles in complex multi-step processes such as DNA repair and activation of NF-KB a master regulator of inflammation. RING-type E3s and their substrates are implicated in a wide variety of human diseases ranging from viral infections to neurodegenerative disorders to cancer. The CpG site, cg23008153, is a probe mapping to the N-shore of the RNFI 80 gene.

FIG. 4N illustrates a genomic diagram 474 of chromosome 18. At location 476 is the SMAD Family Member 2 (SMAD2) gene. The CpG site, cg17243289, is a probe mapping to the SMAD2 gene.

Figure 5:
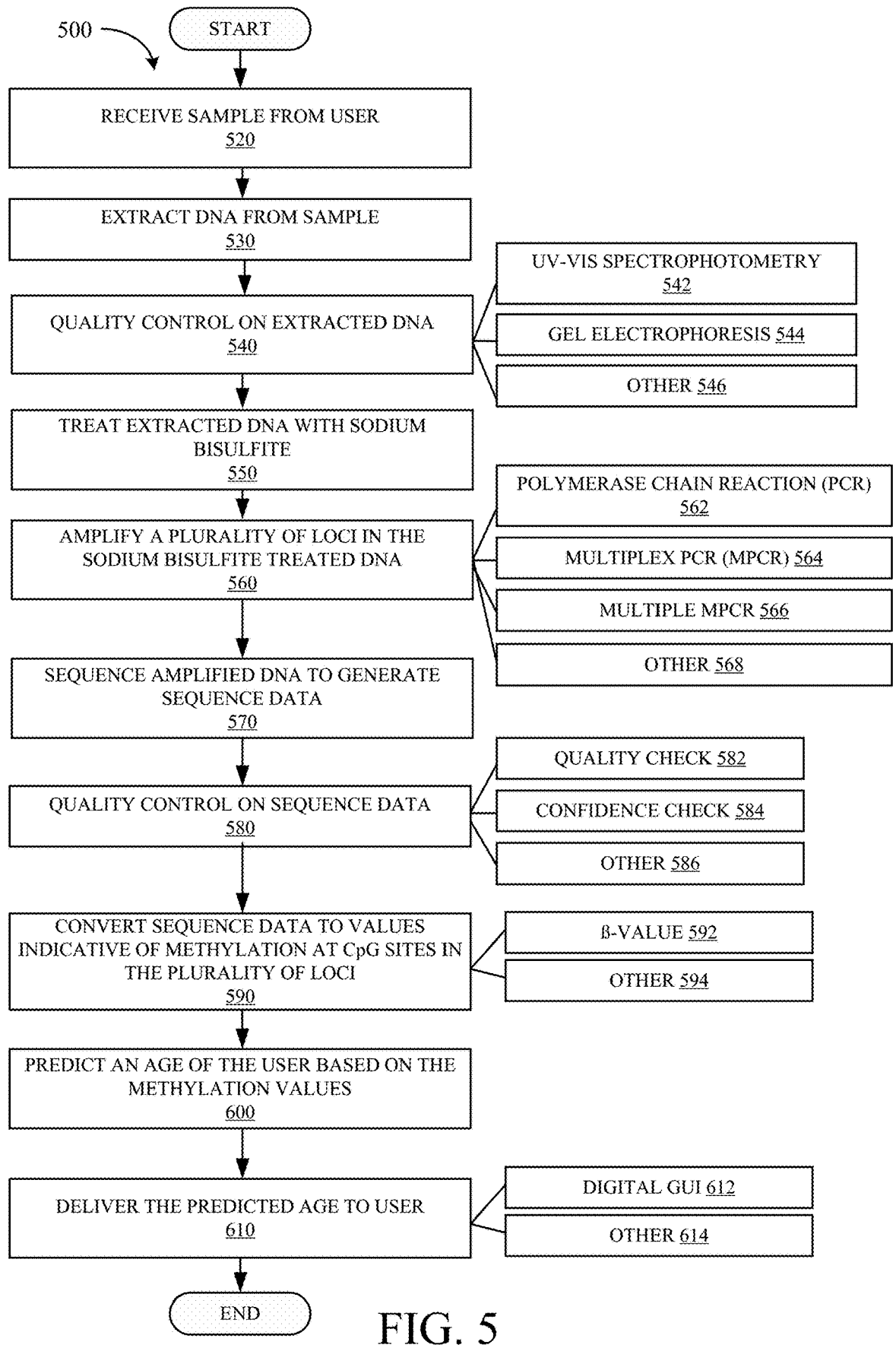
FIG. 5 illustrates a flow diagram showing an example operation of processing a sample to provide an epigenetic age to a user.

FIG. 5 illustrates a flow diagram showing an example operation 500 of processing a sample to provide the epigenetic age to a user. Operation 500 begins at block 520 where a sample from the user is received. The sample may be received by a delivery or shipment in which the user generates a sample and prepares it for transit. For example, the sample may be received in a similar manner to the method discussed below with respect to FIG. 7. In another example, the user may directly deliver the generated sample to the site of DNA extraction, or to a facility that prepares it for preservation during long-term transit. In one embodiment, the sample may be a blood sample. However, it is expressly contemplated that other samples may be received and processed as well.

The operation proceeds at block 530, where DNA is extracted from the sample. The process of DNA extraction includes breaking, or lysing, the cells contained in the sample to release the DNA. Cells may be lysed, for example, by using a lysis buffer or other solution suitable for breaking down cellular membranes while retaining DNA quality. After lysing the cells, the DNA is solubilized and separated from cellular debris. Solubilizing may include, for example, resuspending the lysed DNA in a buffer and/or soluble solution. The cellular debris removed may include proteins, cellular membranes, lipids, or other cellular components that may hinder DNA purity. Separation of the DNA from cellular debris may be done by a variety of methods, including filtration, protein degradation, or any combination thereof. In one embodiment, DNA may be extracted manually. However, in other embodiments, a commercially available DNA extraction kit may be utilized as well.

Operation 500 proceeds at block 540, where quality control is performed on the extracted DNA to receive quality-controlled DNA (QCDNA). Quality control may, for example, include obtaining absorbance measurements of the extracted DNA by ultraviolet-visible (UV-Vis) spectrophotometry 542. The absorbance measurements may be indicative of extracted DNA quality. Additionally, the measurements provided by UV-Vis spectrophotometry 542 may be indicative of the concentration of DNA acquired in the extraction process of the sample. Alternatively, or additionally, quality control may include performing gel electrophoresis on the extracted DNA 544 to provide an indication of DNA quality. For example, DNA may be observed as it travels down the gel to indicate that the DNA is of an expected size and/or quality. Additionally, it is expressly contemplated that other forms of quality control may implemented as well, as indicated by block 546. In one example, quality control may include combining subsequent extracted DNA aliquots in order to achieve a desired concentration level. Additionally, quality control may include combining the extracted DNA of subsequent samples acquired by the user. In another embodiment, quality control may include diluting the extracted DNA in order to achieve a desired DNA concentration.

Operation 500 proceeds at block 550 with treating the extracted DNA with sodium bisulfite. Sodium bisulfite converts cytosine into uracil in the extracted DNA sample, but leaves methylated cytosine (e.g., 5-methylcytosine) unaffected. This, in turn, allows for methylated cytosine to be differentiated from unmethylated cytosine in DNA analysis. In this way, the remaining methylated cytosine within the DNA segment of interest will remain detectable and observable, while unmethylated cytosine will not be in a chemical configuration to distort DNA analysis. Additionally, while sodium bisulfite is used in the present example, it is expressly contemplated that other means of treating the extracted DNA may be utilized as well (e.g., enzyme-based conversion or other methods).

Operation 500 proceeds at block 560, where a plurality of loci in the sodium bisulfite treated DNA is amplified. A locus is defined as a specific position on the DNA where a particular gene or DNA sequence is located. For example, the plurality of loci may be positions including one or more CpG sites of interest. DNA amplification involves generating multiple copies of the loci in one or more DNA segments of interest. As indicated by block 562, amplification of the plurality of loci in the sodium bisulfate treated DNA may occur via polymerase chain reaction (PCR). PCR is a technique involving a set of primers, which are short segments of DNA that define the specific DNA sequence of interest and prepare it for amplification. Once the specific primers indicative of the site(s) to be amplified have been added, a replication enzyme, DNA polymerase, attaches to the site of amplification at the primers, and amplification of the loci in the treated DNA begins under standard reaction conditions. In this way, the one or more sets of primers serve as a marker for the start and end of a target sequence to be amplified.

As indicated by block 564 and further described below with respect to FIG. 6, amplification of the plurality of loci in the sodium bisulfite treated DNA may also occur by multiplex PCR (MPCR). Whereas standard PCR typically involves the use of one pair of primers, MPCR involves the use of two or more primer pairs in the reaction. In this way, a plurality of loci in the DNA segment of interest may be amplified in a single reaction mixture. The plurality of loci may include, for example, a plurality of CpG sites. The plurality of CpG sites within the DNA segment may be amplified in the same reaction mixture using a plurality of primers corresponding to the CpG sites of interest. Additionally, as indicated by block 566, multiple MPCR reactions may be utilized in a single reaction mixture, wherein multiple sites of interest may be amplified in multiple segments of DNA within the mixture. For example, different segments of DNA including a plurality of different CpG sites of interest may be amplified via MPCR in a single reaction mixture to generate amplified DNA corresponding to the plurality of CpG sites. In another example, a plurality segments may be amplified via MPCR in multiple subsequent reactions such that the sites of interest are amplified while the possibility of cross hybridization and/or mis-priming is minimized. In this way, multiple DNA segments of interest, such as those including CpG sites, may be amplified in one or few reactions, thus increasing efficiency and preventing the need to undergo a new reaction per site. Additionally, it is expressly contemplated that other modes of amplifying a plurality of loci can be utilized as well, as indicated by block 568.

The operation proceeds at block 570, where the amplified DNA is sequenced to generate sequence data. Sequencing is the process of determining the specific order, or sequence, of nucleotide bases within the one or more segments of amplified DNA. Sequencing may occur, for example, using a DNA sequencing system, in which the amplified DNA is processed to emit one or more signals indicative of the chain of nucleotides present within the sample. As indicated above with respect to block 550, the extracted DNA is treated with sodium bisulfite prior to amplification. In this way, the signals emitted by the sequencing system indicative of cytosine correlate to methylated cytosine (e.g., 5-methylcytosine) rather than unmethylated. Thus, in an example where one or more CpG sites is amplified and consecutively sequenced, the sequence data received may be indicative of the degree of methylation relative to said CpG sites.

The operation proceeds at block 580, where quality control is performed on the received sequence data. In an example where MPCR is utilized involving a plurality of primers, quality control enables confirmation that no errors have occurred during amplification, such as cross hybridization and/or mis-priming. Quality control may include, for example, a quality check, as indicated by block 582. The quality check may include ensuring that the one or more segments of amplified DNA are of proper length. Additionally, the quality check may include comparing the one or more segments of amplified DNA with a reference to ensure that the proper DNA segment was amplified, and no random sequencing occurred beyond the desired segment(s) of interest. In one embodiment, quality control may further include a confidence check, as indicated by block 584. The confidence check may include, for example, providing a confidence metric indicative of the error rate between the received sequencing data relative to the one or more amplified sites and a reference. Additionally, it is expressly contemplated that other forms of quality control can occur as well, as indicated by block 586.

The operation proceeds at block 590, where the sequence data is converted to values indicative of methylation at the CpG sites in the plurality of loci. Sequence data may be converted to methylation values in a number of different formats. For example, one possible format is the conversion of sequence data indicative of methylation at CpG sites of interest to a decimal between zero and one (β-value), as indicated at block 592, where zero is fully unmethylated and one is fully methylated. Additionally, it is expressly contemplated that the sequence data can be converted to other formats as well, as indicated by block 594.

The operation proceeds at block 600, where an epigenetic age of the user is predicted based on the methylation values. The epigenetic age may be predicted by, for example, inputting the methylation values based on the sequence data into an epigenetic age prediction model, such as model 912 discussed below with respect to FIG. 9. In some examples, the methylation values that are input into the model to predict the epigenetic age of the user are based on sequencing data corresponding to the 42 sites indicated in FIG. 9. Additionally, in some implementations, the methylation values input, corresponding to the amplified CpG sites, are in order of their feature importance to the model or in order of the absolute value of their coefficient. Further, in other examples, less methylation values corresponding to less than 42 amplified CpG sites may be input as well.

The operation proceeds at block 610, where the predicated epigenetic age is delivered to the user. The predicated age can be delivered, for example, using a digital graphical user interface (GUI) 612. Additionally, it is expressly contemplated that the predicted age may be delivered to a user by other means as well, as indicated by block 614.

FIGS. 6A-6H illustrate example diagrams showing example amplifications of one or more portions of DNA. FIGS. 6A-6H recite similar features and like components are numbered accordingly. DNA portion 650 illustratively includes DNA strand 651. As recited above, DNA strand 651 comprises a plurality of nucleotide base pairs (not shown), which extend along the length of strand 651. For example, one or more sets of a cytosine nucleotide followed by a guanine nucleotide (e.g. a CpG site) may be disposed within strand 651. In one embodiment, strand 651 may be a DNA segment of interest and have a length of nucleotides relative to the particular DNA segment. However, in other embodiments, strand 651 may be the length of the human genome.

DNA portion 650 further includes a plurality of primer pairs 654-1 and 654-2 generally disposed over varying lengths of strand 651. As illustrated in FIGS. 6A-6H, each primer 654-1 has a consecutive primer 654-2, which act as the start and stop marker for amplification. In this way, primers 654-1 and 654-2 act as a primer pair. As illustrated, the one or more primer pairs 654-1 and 654-2 define amplification site 652. Amplification site 652 includes a section of strand 651 of interest to be amplified. For example, site 652 may include one or more CpG sites of interest to be amplified. Amplification site 652 can be of varying lengths, as defined by the placement of primer pairs 654-1 and 654-2. For example, the amplification site 652 shown in FIG. 6G is of a larger length than site 652 shown in FIG. 6H relative to the placement of primer pairs 654-1 (654-2).

As noted in FIGS. 6A-6H, each strand 651 can include a plurality of primer pairs 654-1 and 654-2, and thus a plurality of amplification sites 652. For instance, FIG. 6A includes 7 primer pairs 654-1 and 654-2, and therefore 7 amplification sites 652. FIG. 6B includes 7 primer pairs 654-1 and 654-2, and therefore 7 amplification sites 652. FIG. 6C includes 5 primer pairs 654-1 and 654-2, and therefore 5 amplification sites 652. FIG. 6D includes 5 primer pairs 654-1 and 654-2, and therefore 5 amplification sites 652. FIG. 6E includes 5 primer pairs 654-1 and 654-2, and therefore 5 amplification sites 652. FIG. 6F includes 5 primer pairs 654-1 and 654-2, and therefore 5 amplification sites 652. FIG. 6G includes 4 primer pairs 654-1 and 654-2, and therefore 4 amplification sites 652. FIG. 6H includes 4 primer pairs 654-1 and 654-2, and therefore 4 amplification sites 652. Additionally, it is expressly contemplated that any of FIGS. 6A-6H could include a different number of primer pairs and therefore a different number of amplification sites as well.

In one example, FIGS. 6A-6H may be representative of multiple MPCR reactions to amplify a plurality of sites corresponding to a plurality of CpG sites. For example, as shown, 8 separate MPCRs may be completed to amplify a total of 42 sites. The 42 sites may correspond to, for example, the 42 CpG sites set forth below with respect to FIG. 9. Additionally, it is expressly contemplated that less MPCR reactions may be completed to amplify the same 42 CpG sites, or a different number of CpG sites. For instance, a different number of primer pairs 654-1 (654-2) may be added to a single MPCR to increase the amplification sites while reducing the subsequent MPCRs needed. In another example, less than the 42 listed CpG sites may be desired for epigenetic age determination, in which case a lower number of primer pairs 654-1 (654-2) may be added relative to the number of CpG sites to be amplified.

Figure 7:
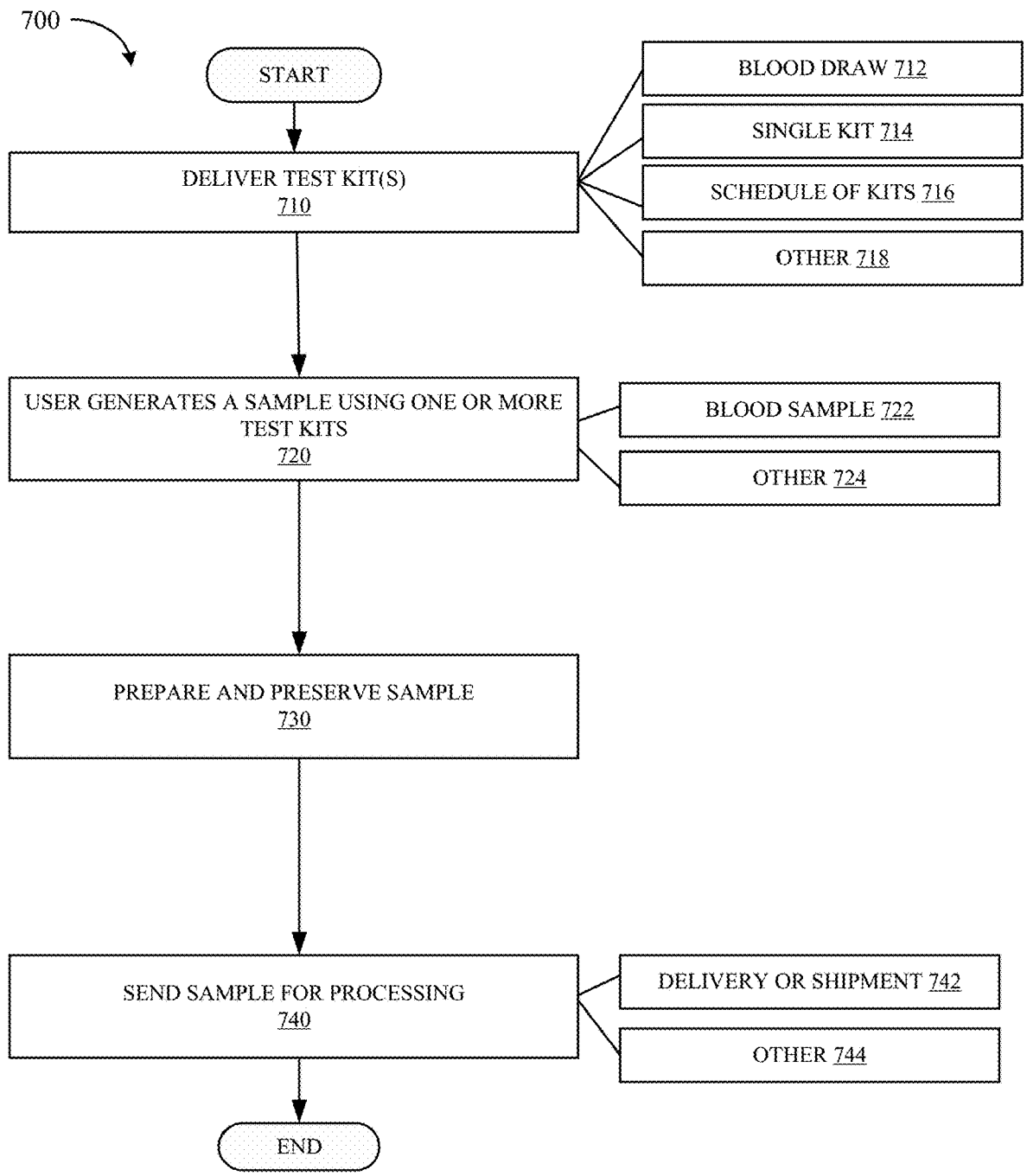
FIG. 7 illustrates a flow diagram showing an example operation of acquiring a sample from a user.

FIG. 7 illustrates a flow diagram showing an example operation of acquiring a sample from a user. Operation 700 begins at block 710 where one or more test kits are delivered to the user. A test kit provides the necessary tools and/or protocols for a user to obtain a sample to be processed. The sample may be obtained in a number of different formats. For example, the sample may be a blood sample obtained by blood draw 712. Blood draw 712 may include any device suitable for safely obtaining blood and retaining sample purity. For example, blood draw 712 may include a non-invasive blood extraction device included in the test kit, in which a user operates the device to obtain the sample. In another example, blood draw 712 may include a vial and syringe. Alternatively, blood draw 712 may include a fingerstick. Additionally, it is expressly contemplated that other samples may be obtained by the user as well. For instance, the sample may be a saliva sample.

As indicated by block 714, delivering the test kit may include delivering a single kit. However, in other examples, the test kit may include multiple test kits. For instance, multiple test kits may be included such that the user may obtain multiple samples to ensure a sample of sufficient quality is acquired. Additionally, as indicated by block 716, delivering the test kit may include delivering a schedule of kits. For example, a plurality of test kits may be scheduled for delivery in specific intervals over time such that a range of samples may be processed to observe the predicted epigenetic age of the user over time. In another example, the schedule of test kits may be delivered to a user at one time with instructions on when to generate and prepare the next consecutive sample. Additionally, the test kit may be some other form of test kit, as indicated by block 718.

Operation 700 proceeds at block 720 where a user generates a sample using the one or more test kits. As indicated by block 722 and further discussed above, the sample generated by the user may be a blood sample. For instance, the sample may be generated using a blood extraction device. The blood sample may be disposed in any vessel suitable for collection. For example, the vessel may be a collection tube provided in the one or more test kits. In one embodiment, the vessel may include one or more indicators to indicate to the user when a sufficient volume of sample has been acquired. For example, the indicator may be a fill line on the lower portion of a collection tube that may indicate to a user that enough sample is collected. In another example, the fill line may be at the middle or near the top of the collection tube. Additionally, the collection tube may contain multiple fill lines corresponding to different volumes of the sample to be collected. For example, a first line on collection tube may indicate that enough sample has been collected for DNA extraction, and an additional line above the first line may indicate that an additional sample aliquot has been collected for a consecutive DNA extraction. Additionally, while a blood sample is described as being generated above, it is expressly contemplated that other samples may be generated by the user as well, as indicated by block 724.

Operation 700 proceeds at block 730 where the sample is preserved and prepared for transit. Preservation of the sample may include sealing the sample in a vessel suitable for transportation. For example, a sample collected in a collection tube may be sealed with a collection tube cap. In another embodiment, preparation of the sample may include freezing the sample prior to transit. Additionally, it is expressly contemplated that other forms of sample preparation can occur as well.

Operation 700 proceeds at block 740 where the sample is sent for processing. The sample may be sent by a delivery or shipment, as indicated by block 742, in which the user generates a sample and stores it and any other necessary contents in an appropriate container for transit. In one example, the container for shipment may be provided in the one or more test kits delivered to the user. However, it is expressly contemplated that other forms of sample transportation can occur as well, as indicated by block 744. For example, the user may directly deliver the generated sample to the site where DNA extraction occurs. Alternatively, the user may deliver the sample to a facility that prepares it for preservation during long-term transit.

Figure 8:
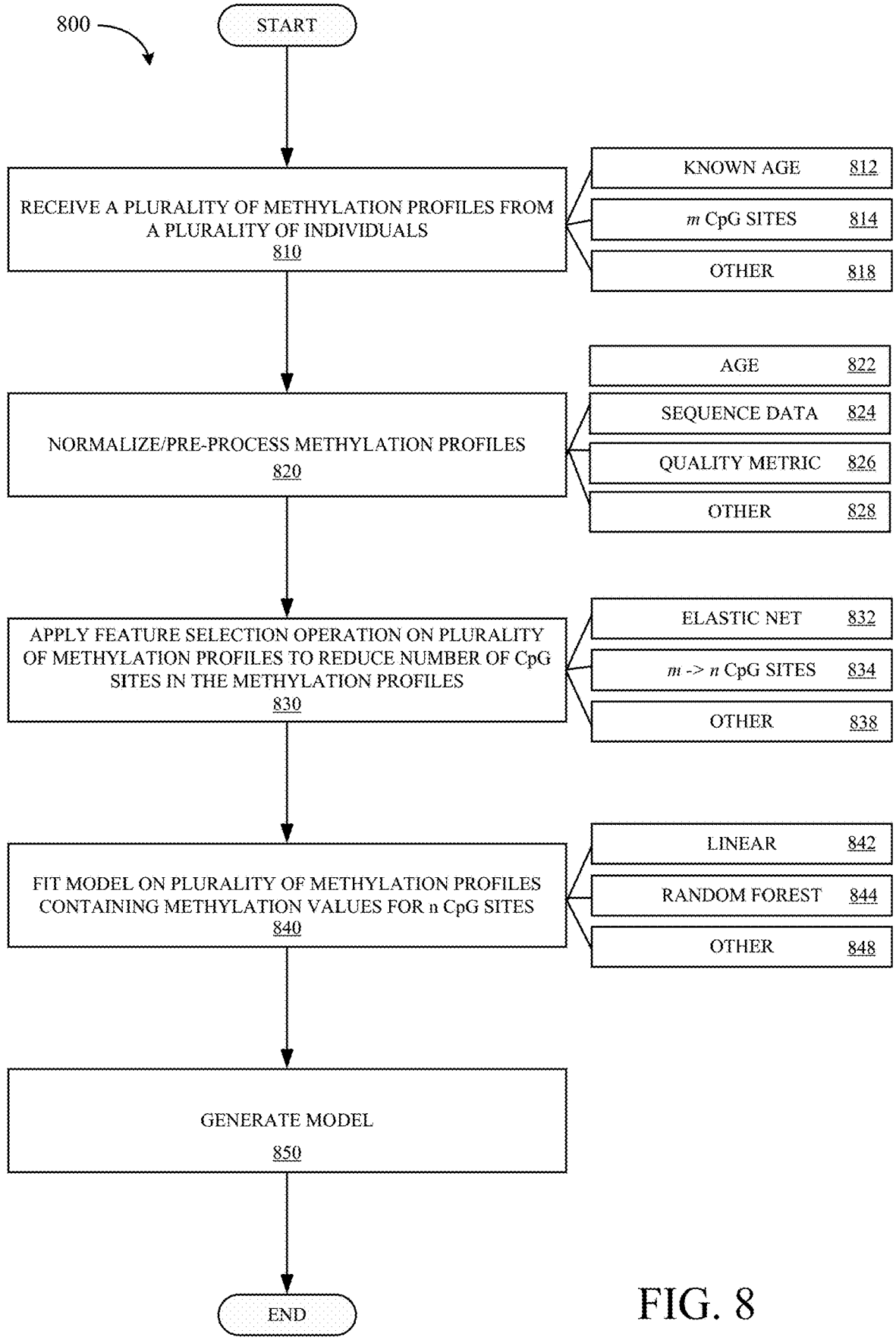
FIG. 8 illustrates a flow diagram showing an example operation of training a model.

FIG. 8 illustrates a flow diagram showing an example operation 800 of training an epigenetic age predicting model. Operation 800 begins at block 810 where a plurality of methylation profiles from a plurality of individuals are received. A methylation profile contains methylation values for a number of CpG sites of the individual. Methylation values can be in a number of different formats. For example, as indicated above, an example format is a decimal between zero and one (B-value), where zero is fully unmethylated and one is fully methylated. These methylation profiles for the individuals can be derived based on the method described above with respect to FIG. 5. For example, the methylation profiles can be obtained by the sequence data acquired via MPCR and sequencing of amplified DNA.

As indicated by block 812, the plurality of individuals' ages are known. This known age can be used to generate the model. For example, the plurality of methylation values in each profile can be used as an input vector and the known age is the scalar output value.

As indicated by block 814, the number of CpG sites determined by the sequence data and in each of the plurality of methylation profiles is m. The quantity m can be a variety of different numbers, as indicated by block 818. For example, m can correspond to a resolution of the methylation analysis method used on the plurality of individuals. For instance, Illumina provides methylation sequencing for 3.3 million or 36 million CpG sites.

Operation 800 proceeds at block 820 where the plurality of methylation profiles received in block 810 are normalized or otherwise pre-processed. As indicated by block 822 the methylation profiles can be normalized based on age. For instance, a specific age range may be overrepresented in the plurality of profiles, therefore the profiles from this age range may need to be weighted less or their chance of being sampled made less likely. In the alternate, a specific age range may be underrepresented in the plurality of profiles, therefore the profiles from this age range may need to be weighted higher or their chance of being sampled made more likely. Additionally, as indicated by block 824, the methylation profiled can be normalized based on sequence data quality. For example, if the sequence data indicates that cross hybridization occurred during MPCR, the methylation values received from this data may need to be weighted less. Additionally, if mis-priming occurred resulting in incorrect amplification, the methylation values received from the sequence data relative to the DNA segment may be discarded.

As indicated by block 826, the plurality of methylation profiles may be curated based on a quality metric. For example, methylation profiles that have a quality metric lower than a threshold are discarded or weighted less than methylation profiles of a higher quality metric. In some examples, the quality metric is indicative of the accuracy of amplification of the plurality of loci. In other examples, the quality metric is indicative of the quality of the sample used in amplification. As indicated by block 828, the plurality of methylation profiles can be normalized or pre-processed in other ways as well.

Operation 800 proceeds at block 830 where a feature selection operation is applied on the plurality of methylation profiles. In some examples, the feature selection is applied on the plurality of methylation profiles after they are pre-processed. In some examples, the feature selection operation is applied on the plurality of methylation profiles received in block 810.

As indicated by block 832, the feature selection operation applied on the plurality of methylation profiles includes elastic net regression. Elastic net regression combines L1 penalties from lasso regression and L2 penalties from ridge regression to reduce the number of CpG sites.

As indicated by block 834, the feature selection applied reduces the number of applicable CpG sites from m to n sites. This reduction can balance dimensionality when there are small number of methylation profiles, but each profile has a large amount of CpG site methylation values. In some examples, m is greater than 100,000. In some examples, m is greater than 400,000. In some examples, m is greater than 800,000. In some examples, n is less than 200. In some examples, n is less than 50. For instance, n may correspond to 42 sites. Additionally, as indicated by block 838, n may correspond to a different number of sites as well.

Operation 800 proceeds at block 840 where a model is fit on the plurality of methylation profiles. In some implementations, the model is fit on the plurality of methylation profiles, but only considers the CpG sites in the subset of n CpG sites. As indicated by block 842, the model can include a linear regression model. As indicated by block 844, the model can include a random forest model. As indicated by block 848, the model can include a different type of model as well.

Operation 800 proceeds at block 850 where the model is generated. In some examples, the model is generated as one or more files that can be imported by other systems which can further train the model or use the model for predictions.

Figure 9:
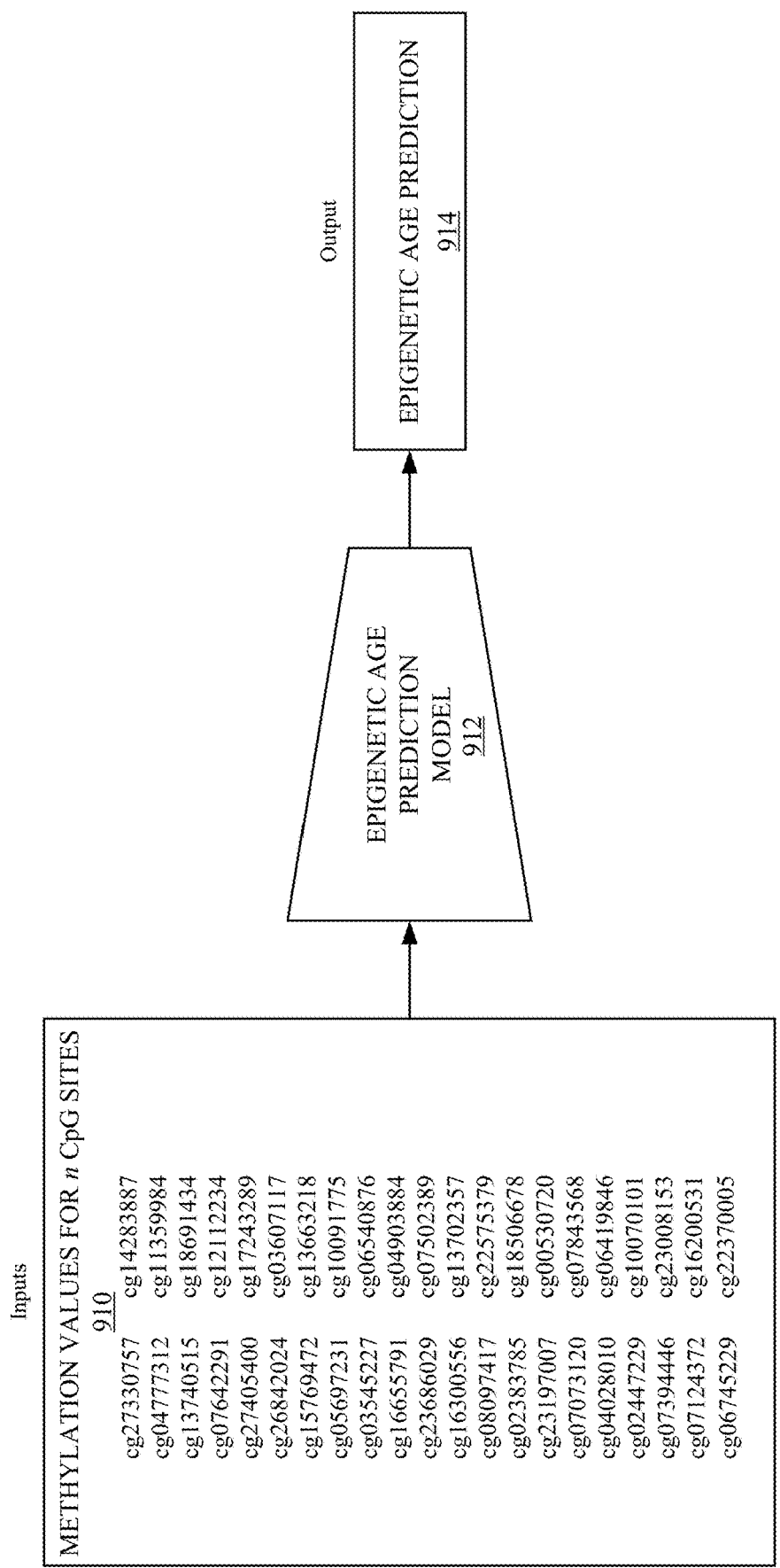
FIG. 9 illustrates a flow diagram showing an example operation of predicting an epigenetic age.

FIG. 9 is a flow diagram showing an example operation of predicting an epigenetic age. Operation 900 begins at block 910 where the input values are received. The input values may be, for example, the values derived from the sequence data indicative of methylation at the CpG sites in the plurality of loci, as noted above with respect to FIG. 5. As shown, there are 42 input values corresponding to the methylation values at 42 different CpG sites. These CpG sites are identified by their CpG cluster identifier number. In some implementations, only a subset of the shown CpG sites is used as inputs. For example, less than 42 of the listed CpG sites may be input relative to the number CpG sites amplified. In some implementations, the shown CpG sites are in order of their feature importance to the model (e.g., in the case of a random forest model) or in order of the absolute value of their coefficient (e.g., in a linear model).

At block 912, the inputs are input into the epigenetic age prediction model. As noted above this model could include a linear regression model (e.g., where each input forms part of a linear expression), random forest model (e.g., where each input forms part of one or more decision trees), or some other type of model. At block 914, the model outputs an epigenetic age prediction.

In some implementations, the model also outputs a confidence score.

Figure 10:
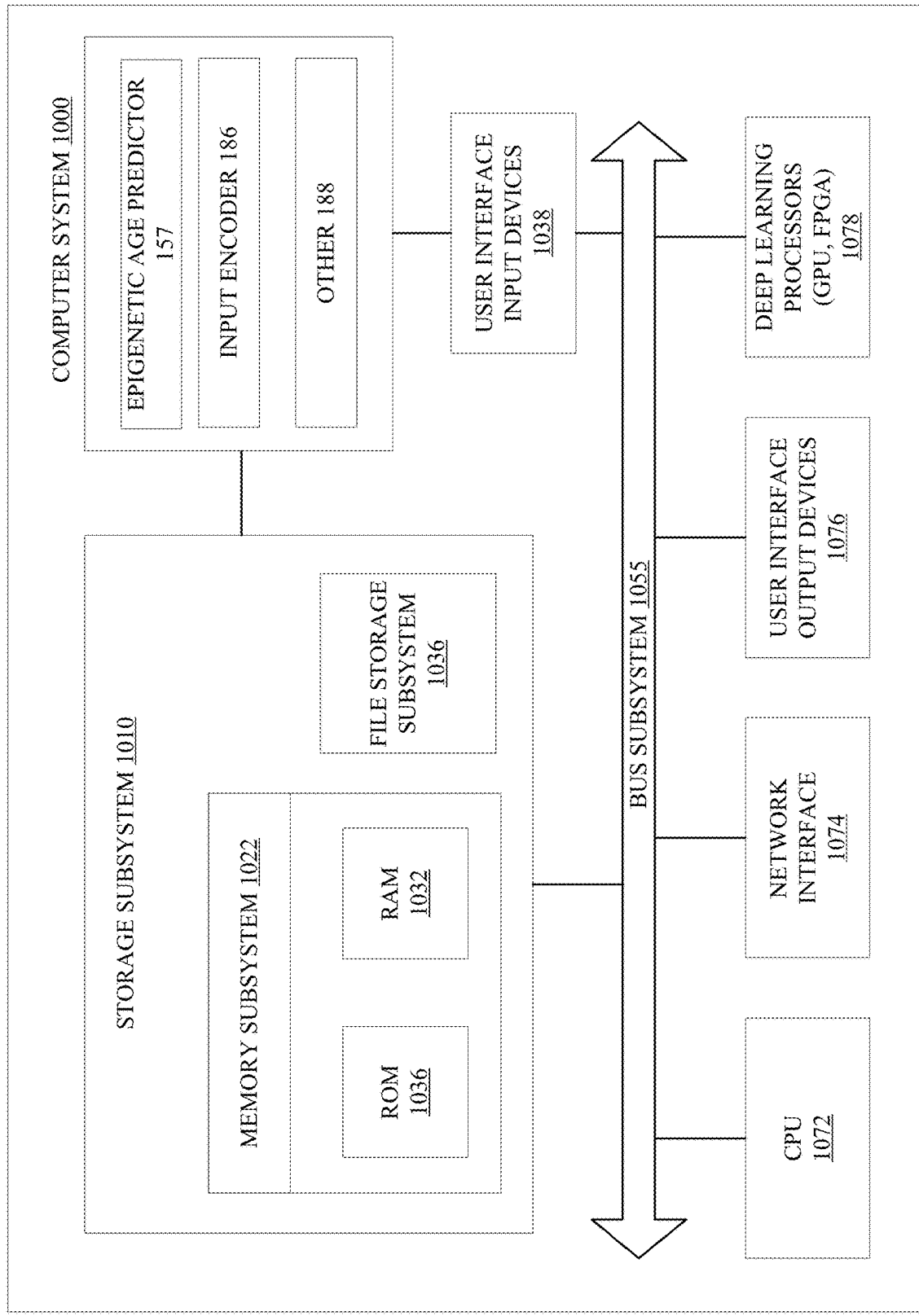
FIG. 10 illustrates a block diagram showing an example computing system.

FIG. 10 is a computer system 1000 that can be used to implement the convolution based base calling and the compact convolution-based base calling disclosed herein. Computer system 1000 includes at least one central processing unit (CPU) 1072 that communicates with a number of peripheral devices via bus subsystem 1055. These peripheral devices can include a storage subsystem 1010 including, for example, memory devices and a file storage subsystem 1036, user interface input devices 1038, user interface output devices 1076, and a network interface subsystem 1074. The input and output devices allow user interaction with computer system 1000. Network interface subsystem 1074 provides an interface to outside networks, including an interface to corresponding interface devices in other computer systems.

In one implementation, the epigenetic age predictor 157 is communicably linked to the storage subsystem 1010 and the user interface input devices 1038. Epigenetic age predictor 157 can include one or more models that receive a plurality of inputs and output an epigenetic age. In some examples, epigenetic age predictor 157 also outputs a confidence score. In one implementation, input encoder 186 pre-processes and/or normalizes inputs before they are fed into a model of epigenetic age predictor. In other implementations, other processing modules 188 can be implemented on the computer system 1000 to execute the technology disclosed.

User interface input devices 1038 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1000.

User interface output devices 1076 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1000 to the user or to another machine or computer system.

Storage subsystem 1010 stores programming and data constructs that provide the functionality of some or all of the modules and methods described herein. These software modules are generally executed by deep learning processors 1078.

Deep learning processors 1078 can include graphics processing units (GPUs), field-programmable gate arrays (FPGAs), application-specific integrated circuits (ASICs), and/or coarse-grained reconfigurable architectures (CGRAs). Deep learning processors 1078 can be hosted by a deep learning cloud platform such as Google Cloud Platform™, Xilinx™, and Cirrascale™. Examples of deep learning processors 1078 include Google's Tensor Processing Unit (TPU)™, rackmount solutions like GX4 Rackmount Series™, GX36 Rackmount Series™, NVIDIA DGX-I™, Microsoft' Stratix V FPGA™, Graphcore's Intelligent Processor Unit (IPU)™ Qualcomm's Zeroth Platform™ with Snapdragon Processors™, NVIDIA's Volta™ NVIDIA's DRIVE PX™ NVIDIA's JETSON TX1/TX2 MODULE™, Intel's Nirvana™, Movidius VPU™ Fujitsu DPI™ ARM's Dynamic1Q™ IBM TrueNorth™ and others.

Memory subsystem 1022 used in the storage subsystem 1010 can include a number of memories including a main random-access memory (RAM) 1032 for storage of instructions and data during program execution and a read-only memory (ROM) 1030 in which fixed instructions are stored. A file storage subsystem 1036 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1036 in the storage subsystem 1010, or in other machines accessible by the processor.

Bus subsystem 1055 provides a mechanism for letting the various components and subsystems of computer system 1000 communicate with each other as intended. Although bus subsystem 1055 is shown schematically as a single bus, alternative implementations of the bus subsystem can use multiple busses.

Computer system 1000 itself can be of varying types including a personal computer, a portable computer, a workstation, a computer terminal, a network computer, a television, a mainframe, a server farm, a widely distributed set of loosely networked computers, or any other data processing system or user device. Due to the ever-changing nature of computers and networks, the description of computer system 1000 depicted in FIG. 10 is intended only as a specific example for purposes of illustrating the preferred implementations of the present invention. Many other configurations of computer system 1000 are possible having more or less components than the computer system depicted in FIG. 10.

We describe various implementations of epigenetic predictors and the training thereof. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections these recitations are hereby incorporated forward by reference into each of the following implementations.

In one implementation, we disclose a method of generating an epigenetic age prediction. The method includes providing a sample extraction test kit. The method includes receiving a sample extracted by the sample extraction test kit. The method includes extracting DNA from the sample. The method includes processing the DNA to receive processed DNA. The method includes amplifying a plurality of loci in the processed DNA to receive amplified DNA. The method includes processing the amplified DNA to receive a plurality of methylation values for one or more CpG sites in the plurality of loci.

In one implementation, amplifying the plurality of loci in the processed DNA in the method includes performing a polymerase chain reaction (PCR) to receive the amplified DNA.

In one implementation, amplifying the plurality of loci in the processed DNA in the method includes performing a multiplex polymerase chain reaction (MPCR) to receive the amplified DNA.

In one implementation, performing the MPCR to receive the amplified DNA in the method includes using a plurality of primer pairs with the processed DNA to amplify the plurality of loci.

In one implementation, the plurality of primer pairs in the method correspond to one or more sites in the plurality of loci identified by markers cg27330757, cg04777312, cg13740515, cg07642291 and cg27405400.

In one implementation, the plurality of primer pairs in the method correspond to one or more sites in the plurality of loci identified by markers cg15769472, cg05697231, cg03545227, cg16655791 and cg23686029.

In one implementation, the plurality primer pairs in the method correspond to one or more of sites in the plurality of loci identified by markers cg16300556, cg08097417, cg02383785, cg23197007, cg07073120, cg04028010, cg02447229, cg07394446, cg07124372, cg06745229, cg14283887, cg11359984, cg18691434, cg12112234, cg17243289, cg03607117, cg13663218, cg10091775, cg06540876, cg04903884, cg07502389, cg13702357, cg22575379, cg18506678, cg00530720, cg07843568, cg06419846, cg10070101, cg23008153, cg16200531 and cg22370005.

In one implementation, wherein processing the DNA in the method includes performing quality control on the DNA to receive quality-controlled DNA.

In one implementation, processing the DNA in the method includes treating the quality-controlled DNA with sodium bisulfite to receive treated DNA.

In one implementation, the sample in the method is a blood sample.

In one implementation, the one or more CpG sites in the method include a plurality of CpG sites.

In one implementation, the plurality of CpG sites include 42 sites.

In one implementation, processing the amplified DNA in the method includes sequencing the amplified DNA to obtain sequence data indicative of the plurality of methylation values for the one or more CpG sites.

In one implementation, we disclose a method of generating an epigenetic clock predictor. The method includes receiving a plurality of methylation profiles from a plurality of individuals based on sequence data of the plurality of individuals, the sequence data corresponding to a degree of methylation at a plurality of CpG sites. The method includes training a model based on the plurality of methylation profiles, the model being configured to predict an epigenetic age based on methylation values obtained from the sequence data.

In one implementation, the sequence data in the method corresponds to the degree of methylation at the plurality of CpG sites identified by markers cg27330757, cg04777312, and cg13740515.

In one implementation, the plurality of CpG sites include 42 sites.

In one implementation, the sequence data in the method is generated by amplifying a plurality of loci, the plurality of loci including the plurality of CpG sites.

In one implementation, training the model includes training a linear regression model.

In one implementation, training the model includes training a random forest model.

In one implementation, we disclose a method of generating an epigenetic age prediction. The method includes receiving a sample. The method includes extracting DNA from the sample. The method includes treating the DNA with sodium bisulfite to receive treated DNA. The method includes amplifying a plurality of loci in the treated DNA using a plurality of primer pairs to receive a plurality of amplified DNA strands, the plurality of amplified DNA strands including one or more CpG sites. The method includes sequencing the plurality of amplified DNA strands to receive sequence data indicative of methylation at the one or more CpG sites. The method includes processing the sequence data to receive a plurality of methylation values for the one or more CpG sites.

Although the present invention has been described with reference to preferred embodiments, workers skilled in the art will recognize that changes may be made in form and detail without departing from the spirit and scope of the invention.

What is claimed is:

1. A method of obtaining information useful to determine an age of an individual, the method comprising actions of:
    receiving a sample of blood extracted by a finger prick sample extraction test kit;
    extracting DNA from the sample; and
    processing a plurality of loci in the DNA by applying a polymerase chain reaction (PCR)-based method to determine methylation values for 42 or more CpG sites in the plurality of loci;
    wherein two or more sites in the plurality of loci are identified by markers cg27330757, cg04777312, cg13740515, cg07642291, cg27405400, cg15769472, cg05697231, cg03545227, cg16655791, cg23686029, cg16300556, cg23197007, cg07073120, cg04028010, cg02447229, cg07394446, cg07124372, cg06745229, cg14283887, cg11359984, cg18691434, cg12112234, cg17243289, cg13663218, cg10091775, cg06540876, cg04903884, cg07502389, cg13702357, cg22575379, cg18506678, cg00530720, cg07843568, cg10070101, cg23008153, cg16200531 and cg22370005;
    so that information useful to determine an epigenetic age of the individual is obtained.

2. The method of claim 1, further including:
    processing the plurality of loci by applying multiplex polymerase chain reactions (MPCR) that exposes the DNA to a plurality of primer pairs in a single reaction mixture to amplify a subset of the CpG sites; and
    performing a plurality of MPCRs for the sample.

3. The method of claim 2, wherein the plurality of primer pairs corresponds to two or more further sites, for a total of at least four sites in the plurality of loci identified by the markers listed.

4. The method of claim 3, further including calculating the epigenetic age of the individual using at least the information obtained.

5. The method of claim 3, wherein the plurality of primer pairs corresponds to two or more further sites, for a total of at least six sites in the plurality of loci identified by the markers listed.

6. The method of claim 5, further including calculating the epigenetic age of the individual using at least the information obtained.

7. The method of claim 1, further including processing the DNA further by performing quality control on the DNA to produce quality-controlled DNA.

8. The method of claim 7, further including treating the quality-controlled DNA further with sodium bisulfite to produce treated DNA.

9. The method of claim 1, further including processing amplified DNA to obtain sequence data indicative of the plurality of methylation values for amplified CpG sites.

* * * * *